US000001992B1

(19) United States

(12) Statutory Invention Registration

Bender et al.

(10) Reg. No.: US H1992 H

(43) Published: Sep. 4, 2001

(54) METALLOPROTEINASE INHIBITORS, PHARMACEUTICAL COMPOSITIONS CONTAINING THEM, AND THEIR PHARMACEUTICAL USES

(75) Inventors: Steven L. Bender, Oceanside, CA (US); Arlindo L. Castelhano, New City, NY (US)

(73) Assignee: Agouron Pharmaceuticals, Inc., La Jolla, CA (US)

(21) Appl. No.: 09/372,064

(22) Filed: Aug. 11, 1999

Related U.S. Application Data

(63) Continuation of application No. 09/073,240, filed on May 6, 1998, now abandoned.

(60) Provisional application No. 60/045,931, filed on May 9, 1997.

(51) Int. Cl.[7] ..... C07D 211/32; C07D 261/06; A01K 31/55

(52) U.S. Cl. ..... 546/234; 546/337; 546/221; 548/247; 548/338.1; 514/212; 514/330; 514/318

*Primary Examiner*—Peter A. Nelson

(74) *Attorney, Agent, or Firm*—Fitzpatrick, Cella, Harper & Scinto

(57) ABSTRACT

The present invention relates to compounds of formula I:

(I)

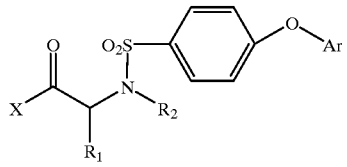

wherein Ar is an aryl group or a heteroaryl group; X is —NH—OH or —OH; $R_1$ is H, —CH($R_3$)($R_4$), —C(O)$R_3$, a cycloalkyl group, a heterocycloalkyl group, an aryl group, or a heteroaryl group, wherein $R_3$ is H or any suitable substituent and $R_4$ is H, an alkyl group, a cycloalkyl group, a heterocycloalkyl group, an aryl group, or a heteroaryl group; $R_2$ is $CH_2$-$R_5$, wherein $R_5$ is H or any suitable substituent, or wherein $R_5$ and $R_4$ are optionally substituted carbon atoms singly- or double-bonded to one another; and pharmaceutically acceptable prodrugs, salts, and solvates thereof. The invention further relates to methods of using these compounds, particularly as metalloproteinase inhibitors.

26 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METALLOPROTEINASE INHIBITORS, PHARMACEUTICAL COMPOSITIONS CONTAINING THEM, AND THEIR PHARMACEUTICAL USES

RELATED APPLICATION DATA

This application is a continuation of U.S. patent application Ser. No. 09/073,240, filed May 6, 1998, now abandoned and claims priority benefits under 35 U.S.C. §119, and any other applicable treaty, statutes, or regulations, based on U.S. Provisional patent application Ser. No. 60/045,931, filed May 9, 1997. These afore-mentioned applications are entirely incorporated herein by reference.

Additionally, the subject matter of this application relates to the invention of Steven L. Bender and Melwyn A. Abreo described in U.S. Provisional patent application Ser. No. 60/041,821 (filed Apr. 1, 1997) and U.S. patent application Ser. Nos. 08/825,318 (filed Apr. 1, 1997) and 09/049,949 (filed Mar. 30, 1998; attorney docket number 01074.0173-01000). Each of these applications is entitled "Metalloproteinase Inhibitors, Pharmaceutical Compositions Containing Them and Their Pharmaceutical Uses," and each application is entirely incorporated herein by reference.

BACKGROUND AND DESCRIPTION OF THE INVENTION

The present invention relates to compounds that inhibit metalloproteinases, particularly matrix metalloproteinases and tumor necrosis factor-α convertase, and their pharmaceutically acceptable salts and pharmaceutically acceptable prodrugs. The invention further relates to the uses of these compounds, salts, and prodrugs for the therapeutic treatment of humans or animals.

Matrix metalloproteinases ("MMPs") are a family of enzymes, including, but not limited to, collagenases, gelatinases, matrilysin, and stromelysins, which are involved in the degradation and remodeling of connective tissues. These enzymes are found in a number of cell types that are found in or associated with connective tissue, such as fibroblasts, monocytes, macrophages, endothelial cells, and metastatic tumor cells. They also share a number of properties, including zinc and calcium dependence, secretion as zymogens, and 40–50% amino acid sequence homology.

Matrix metalloproteinases degrade the protein components of the extracellular matrix, i.e., the protein components found in the linings of joints, interstitial connective tissue, basement membranes, cartilage, and the like. These proteins include collagen, proteoglycan, fibronectin, and lamanin.

Collagen is the major structural protein of mammalian tissue, comprising one-third of the total protein in mammalian organisms, and it is an essential component of many matrix tissues, including cartilage, bone, tendons, and skin. Interstitial collagenases catalyze the initial (rate-limiting) cleavage of native collagen types I, II, III, and X. These enzymes cleave collagen into two fragments which spontaneously denature at physiological temperature. Denaturation of collagen involves conversion of the rigidly coiled helix to a random coil referred to as gelatin. These gelatin (denatured collagen) fragments are then subject to further cleavage and degradation by less specific enzymes. The net result of collagenase cleavage is thus the loss of structural integrity in the matrix tissue (collagen collapse), an essentially irreversible process.

The gelatinases include two distinct yet highly related enzymes: a 72-kiloDalton (kDa) enzyme and a 92-kiloDalton enzyme. The former is released by fibroblasts while the latter is released by mononuclear phagocytes, neutrophils, corneal epithelial cells, tumor cells, cytotrophoblasts, and keratinocytes. Both enzymes degrade gelatins (denatured collagens), collagen types IV (basement membrane) and V, fibronectins (high molecular weight multifunctional glycoproteins found in soft connective tissue and basement membranes), and insoluble elastin (highly cross-linked hydrophobic proteins found in load bearing fibers of mammalian connective tissue).

Stromelysins (1 and 2) cleave a broad range of matrix substrates, including lamanin, fibronectins, proteoglycans, and collagen types IV and IX (non-helical).

Matrilysin (putative metalloproteinase or PUMP) also degrades a wide variety of matrix substrates, including proteoglycans, gelatins, fibronectins, elastins, and lamanin. Matrilysin has been found in mononuclear phagocytes, rat uterine explants, and tumor cells.

In normal tissues, the activity of matrix metalloproteinases is tightly regulated. As a result, the breakdown of connective tissue mediated by these enzymes is generally in a dynamic equilibrium with synthesis of new matrix tissue.

In a number of pathological disease conditions, however, deregulation of matrix metalloproteinase activity leads to the uncontrolled breakdown of extracellular matrix. These disease conditions include arthritis (e.g., rheumatoid arthritis and osteoarthritis), periodontal disease, aberrant angiogenesis, tumor metastasis and invasion, tissue ulceration (e.g., corneal ulceration, gastric ulceration, or epidermal ulceration), bone disease, HIV-infection, and complications from diabetes.

Administration of matrix metalloproteinase inhibitors has been found to reduce the rate of connective tissue degradation, thereby leading to a favorable therapeutic effect. For example, in *Cancer Res.,* vol. 53, p. 2087 (1993), a synthetic matrix metalloproteinase inhibitor was shown to have in vivo efficacy in a murine model for ovarian cancer with an apparent mode of action consistent with inhibition of matrix remodeling. The design and uses of MMP inhibitors are reviewed, for example, in *J. Enzyme Inhibition,* 2, 1–22 (1987); *Progress in Medicinal Chemistry* 29, 271–334 (1992); *Current Medicinal Chemistry,* 2, 743–762 (1995); *Exp. Opin. Ther. Patents,* 5, 1287–1296 (1995); and *Drug Discovery Today,* 1, 16–26 (1996).

Matrix metalloproteinase inhibitors are also the subject of numerous patents and patent applications, including: U.S. Pat. No. 5,189,178; U.S. Pat. No. 5,183,900; U.S. Pat. No. 5,506,242; U.S. Pat. No. 5,552,419; U.S. Pat. No. 5,455,258; European Patent Application No. 0 438 223; European Patent Application No. 0 276 436; WIPO International Publication No. WO 92/21360; WIPO International Publication No. WO 92/06966; WIPO International Publication No. WO 92/09563; WIPO International Publication No. WO 96/00214; WIPO International Publication No. 95/35276; WIPO International Publication No. WO 96/27583, WIPO International Publication No. WO 96/33172, European Patent Application No. 0 757 984, and European Patent Application No 0 757 037.

Tumor necrosis factor-α ("TNF-α") is a cytokine which is produced as a 28-kDa precursor and released in an active 17-kDa form. This active form can mediate a large number of deleterious effects in vivo, including inflammation, fever, cardiovascular effects, haemorrhage, coagulation, and acute phase responses, similar to those seen during acute infections and shock states. Chronic administration of TNF-α can cause cachexia and anorexia; accumulation of excess of TNF-α can be fatal.

TNF-α convertase is a metalloproteinase involved in the biosynthesis of TNF-α. Inhibition of TNF-α convertase inhibits production of TNF-α.

Since excessive TNF-α production has been noted in several disease conditions characterized by MMP-mediated tissue degradation, including multiple sclerosis, arthritis, and cancer, compounds which inhibit both MMPs and TNF-α convertase are especially advantageous for the treatment or prophylaxis of disease conditions in which both mechanisms are involved. Although compounds that both inhibit MMP activity and TNF-α production have been disclosed in WIPO International Publication Nos. WO 94/24140 and WO 94/02466, there is still a need for effective MMP and/or TNF-α convertase inhibiting agents.

Because of their beneficial therapeutic effects, there is a need for effective inhibitors of metalloproteinase activity. The present invention is therefore directed to certain compounds that inhibit metalloproteinases, such as MMPs and TNF-α convertase, their pharmaceutically acceptable prodrugs, salts, and solvates, pharmaceutical compositions containing the same, and methods of using the same, as well as to methods and intermediates useful in their preparation. Additional features and advantages of the invention will be set forth in the description which follows, and in part will be apparent from the description or may be learned from practice of the invention.

To achieve these and other advantages, the present invention provides a compound of formula I:

(I)

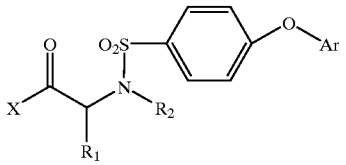

wherein Ar is an aryl group or a heteroaryl group; X is —NH—OH or —OH; $R_1$ is H, —CH($R_3$)($R_4$), —C(O)$R_3$, a cycloalkyl group, a heterocycloalkyl group, an aryl group, or a heteroaryl group, wherein $R_3$ is H or any suitable substituent and $R_4$ is H, an alkyl group, a cycloalkyl group, a heterocycloalkyl group, an aryl group, or a heteroaryl group; $R_2$ is $CH_2$-$R_5$, wherein $R_5$ is H or any suitable substituent, or wherein $R_5$ and $R_4$ are optionally substituted carbon atoms singly- or double-bonded to one another; or a pharmaceutically acceptable prodrug, salt, or solvate thereof.

The present invention also is directed to a pharmaceutical composition comprising (a) a therapeutically effective amount of a compound of formula (I) or a pharmaceutically acceptable prodrug, salt, or solvate thereof; and (b) a pharmaceutically acceptable carrier, diluent, vehicle, or excipient.

The present invention is further directed to a method of treating a mammalian disease condition mediated by metalloproteinase activity which comprises administering to a mammal in need thereof a therapeutically effective amount of a compound of formula I or a pharmaceutically acceptable prodrug, salt, or solvate thereof. The compound of formula I (or its pharmaceutically acceptable prodrug, salt, or solvate) may be administered in the form of a pharmaceutical composition, as described above. Additionally, the present invention is directed to a method of treating tumor growth, invasion, or metastasis; osteoarthritis; rheumatoid arthritis; osteoporosis; periodontitis; gingivitis; chronic dermal wounds; corneal ulceration: degenerative skin disorders; multiple sclerosis; stroke; atherosclerosis; glomerular disease; or a disease condition characterized by unwanted angiogenesis, such as diabetic retinopathy, macular degeneration, angiofibromas, or hemangiomas.

The present invention is still further directed to a method of inhibiting the activity of a metalloproteinase that comprises contacting the metalloproteinase with an effective amount of a compound of formula (I) or a pharmaceutically acceptable prodrug, salt, or solvate thereof, optionally, in the form of a pharmaceutical composition as described above.

As used in the present application, the following definitions apply, unless otherwise indicated:

An "alkyl group" is intended to mean a straight or branched chain monovalent radical of saturated and/or unsaturated carbon atoms and hydrogen atoms, such as methyl, ethyl, propyl, isopropyl, butyl, isobutyl, t-butyl, ethenyl, pentenyl, butenyl, propenyl, ethynyl, butynyl, propynyl, pentynyl, hexynyl, and the like, which may be unsubstituted (i.e., containing only carbon and hydrogen) or substituted by one or more suitable substituents as defined below.

An "O-alkyl group" or "alkoxy group" is intended to mean an oxygen bonded to an alkyl group, wherein the alkyl group is as defined above.

A "cycloalkyl group" is intended to mean a non-aromatic, monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more suitable substituents. Illustrative examples of cycloalkyl groups include, but are not limited to, cyclopropyl, cyclobutyl, cyclopentyl, cyclopentenyl, cyclohexyl, cyclohexenyl, cycloheptyl, cyclooctyl, bicyclo[2.2.1.]heptyl, bicyclo[2.2.1.]hept-2-en-5-yl, bicyclo[2.2.2]octyl, bicyclo[3.2.1.]nonyl, bicyclo[4.3.0]nonyl, bicyclo[4.4.0]decyl, indan-1-yl, indan-2-yl, tetralin-1-yl, tetralin-2-yl, adamantyl, and the like.

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen, and sulfur, wherein the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl, 1,5,9-triazacyclododecyl, and the like.

An "aryl group" is intended to mean an aromatic, monovalent monocyclic, bicyclic, or tricyclic radical containing 6, 10, 14, or 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, phenyl, naphthyl, fluoren-2-yl, indan-5-yl, and the like.

A "heteroaryl group" is intended to mean an aromatic monovalent monocyclic, bicyclic, or tricyclic radical containing 5, 6, 7, 8, 9, 10, 11, 12, 13, 14, 15, 16, 17, or 18 ring atoms, including 1, 2, 3, 4, or 5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include, but are not limited to, pyrrolyl, imidazolyl, pyrazolyl, furyl, thienyl, thiazolyl, oxazolyl, isoxazolyl, isothiazolyl, oxadiazolyl, triazolyl, tetrazolyl, pyrazinyl, pyridyl, pyrimidyl, pyridazinyl, indolyl, isoindolyl, benzimidazolyl, benzofuryl, isobenzofuryl, benzothienyl, quinolyl, isoquinolyl, phthalazinyl, carbazolyl, purinyl, pteridinyl, acridinyl, phenanthrolinyl, phenoxazinyl, phenothiazinyl, and the like.

An "acyl group" is intended to mean a —C(O)—$R_5$— radical, wherein $R_5$ is any suitable substituent as defined below.

A "sulfonyl group" is intended to mean a —S(O)(O)—$R_5$— radical, wherein $R_5$ is any suitable substituent as defined below.

The term "suitable substituent" is intended to mean any of the substituents recognizable to those skilled in the art as not adversely affecting the inhibitory activity of the inventive compounds. Illustrative examples of suitable substituents include, but are not limited to, oxo groups, alkyl groups, hydroxy groups, halo groups, cyano groups, nitro groups, cycloalkyl groups, heterocycloalkyl groups, aryl groups, heteroaryl groups, trialkylsilyl groups, groups of formula (A)

(A)

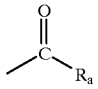

wherein $R_a$ is hydrogen, an alkyl group, a cycloalkyl group, a heterocycloalkyl group, an aryl group, or a heteroaryl group, groups of formula (B)

(B)

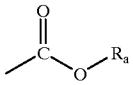

wherein $R_a$ is hydrogen, an alkyl group, a cycloalkyl group, a heterocycloalkyl group, an aryl group, or a heteroaryl group, groups of formula (C)

(C)

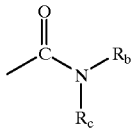

wherein $R_b$ and $R_c$ are independently hydrogen, an alkyl group, a cycloalkyl group, a heterocycloalkyl group, an aryl group, or a heteroaryl group, groups of formula (D)

(D)

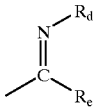

wherein $R_d$ is hydrogen, an alkyl group, a cycloalkyl group, a heterocycloalkyl group, an aryl group, a heteroaryl group, a hydroxy group, an alkoxy group, an amino group, an alkylamino group, a dialkylamino group, or an acylamino group; and $R_e$ is hydrogen, an alkyl group, a cycloalkyl group, a heterocycloalkyl group, an aryl group, a heteroaryl group, an amino group, an alkylamino group, or a dialkylamino group, groups of formula (E)

(E)

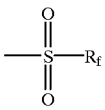

wherein $R_f$ is an alkyl group, a cycloalkyl group, a heterocycloalkyl group, an aryl group, or a heteroaryl group, groups of formula (F)

(F)

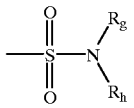

wherein $R_g$ and $R_h$ are independently hydrogen, an alkyl group, a cycloalkyl group, a heterocycloalkyl group, an aryl group, or a heteroaryl group, groups of formula (G)

(G)

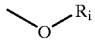

wherein $R_i$ is an alkyl group, a cycloalkyl group, a heterocycloalkyl group, an aryl group, a heteroaryl group, or a group of formula (A), formula (B), formula (C), formula (H) (defined below), or formula (K) (defined below), groups of formula (H)

(H)

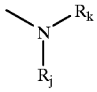

wherein $R_j$ is hydrogen, an alkyl group, a cycloalkyl group, a heterocycloalkyl group, an aryl group, a heteroaryl group, a hydroxy group, an alkoxy group, an amino group, or a group of formula (A), formula (B), formula (C) or formula (D); and wherein $R_k$ is hydrogen, an alkyl group, a cycloalkyl group, a heterocycloalkyl group, an aryl group, a heteroaryl group, or a group of formula (A), formula (B), formula (C), formula (D), formula (E), or formula (F), groups of formula (J)

(J)

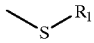

wherein $R_l$, is hydrogen, an alkyl group, a cycloalkyl group, a heterocycloalkyl group, an aryl group, a heteroaryl group, or a group of formula (C), and groups of formula (K)

(K)

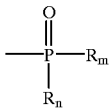

wherein $R_m$ and $R_n$ are independently an alkyl group, a cycloalkyl group, a heterocycloalkyl group, an aryl group, a heteroaryl group, a hydroxy group, an alkoxy group, an amino group, an alkylamino group, or a dialkylamino group.

The term "suitable organic moiety" is intended to mean any organic moiety recognizable to those skilled in the art as not adversely affecting the inhibitory activity of the inventive compounds. Illustrative examples of suitable organic moieties include, but are not limited to oxo groups, alkyl groups, hydroxy groups, halo groups, cyano groups, nitro groups, cycloalkyl groups, heterocycloalkyl groups, aryl groups, heteroaryl groups, trialkylsilyl groups, and groups of formulas (A), (B), (C), (D), (E), (F), (G), (H), (J), and (K), as defined above.

A "hydroxy group" is intended to mean the radical —OH.

An "oxo group" is intended to mean the divalent radical =O.

A "halo group" is intended to mean any of the radicals —F, —Cl, —Br, or —I.

A "cyano group" is intended to mean the radical —C≡N.

A "nitro group" is intended to mean the radical $—NO_2$.

A "trialkylsilyl group" is intended to mean the radical $—SiR_pR_qR_s$, where $R_p$, $R_q$, and $R_s$ are each independently an alkyl group.

A "carboxy group" is intended to mean a group of formula (B) wherein $R_a$ is hydrogen.

A "alkoxycarbonyl group" is intended to mean a group of formula (B) wherein $R_a$ is an alkyl group as defined above.

A "carbamoyl group" is intended to mean a group of formula (C) wherein $R_b$ and $R_c$ are both hydrogen.

An "amino group" is intended to mean the radical $—NH_2$.

An "alkylamino group" is intended to mean the radical $—NHR_u$, wherein $R_u$ is an alkyl group as defined above.

A "dialkylamino group" is intended to mean the radical $—NR_uR_v$, wherein $R_u$ and $R_v$, which are the same or different, are each an alkyl group as defined above.

A "pharmaceutically acceptable prodrug" is intended to mean a compound that is converted under physiological conditions or by solvolysis to a compound of formula I.

A "pharmaceutically acceptable solvate" is intended to mean a solvate that retains the biological effectiveness and properties of the biologically active components of compounds of formula I.

Examples of pharmaceutically acceptable solvates include, but are not limited to, compounds of formula I in combination with water, isopropanol, ethanol, methanol, DMSO, ethyl acetate, acetic acid, or ethanolamine.

In the case of solid formulations, it is understood that the inventive compounds may exist in different forms, such as stable and metastable crystalline forms and isotropic and amorphous forms, all of which are intended to be within the scope of the present invention.

A "pharmaceutically acceptable salt" is intended to mean those salts that retain the biological effectiveness and properties of the free acids and bases and that are not biologically or otherwise undesirable.

Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the inventive compound is a base, the desired salt may be prepared by any suitable method known to the art, including treatment of the free base with an inorganic acid, such as hydrochloric acid, hydrobromic acid, sulfuric acid, nitric acid, phosphoric acid, and the like, or with an organic acid, such as acetic acid; maleic acid; succinic acid; mandelic acid; fumaric acid; malonic acid; pyruvic acid; oxalic acid; glycolic acid; salicylic acid; pyranosidyl acids such as glucuronic acid and galacturonic acid; alpha-hydroxy acids such as citric acid and tartaric acid; amino acids such as aspartic acid and glutamic acid; aromatic acids such as benzoic acid and cinnamic acid; sulfonic acids such a p-toluenesulfonic acid or ethanesulfonic acid; or the like.

If the inventive compound is an acid, the desired salt may be prepared by any suitable method known to the art, including treatment of the free acid with an inorganic or organic base, such as an amine (primary, secondary, or tertiary), an alkali metal hydroxide, an alkaline earth metal hydroxide, or the like. Illustrative examples of suitable salts include organic salts derived from amino acids such as glycine and arginine; ammonia; primary, secondary, and tertiary amines; cyclic amines such as piperidine, morpholine, and piperazine; and inorganic salts derived from sodium, calcium, potassium, magnesium, manganese, iron, copper, zinc, aluminum, and lithium.

The inventive compounds may exist as single stereoisomers, racemates, and/or mixtures of enantiomers and/or diastereomers. All such single stereoisomers, racemates, and mixtures thereof are intended to be within the scope of the present invention.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

In the compounds, compositions, and methods of the present invention, preferably $R_3$ is hydrogen, an alkyl group, a cycloalkyl group, a heterocycloalkyl group, an aryl group, a heteroaryl group, —$OR_{10}$, —$SR_{10}$, C≡C—$R_{10}$, —C(O)$OR_{10}$, C(O)$NHR_{10}$, wherein $R_{10}$ is hydrogen, an alkyl group, a cycloalkyl group, a heterocycloalkyl group, an aryl group, or a heteroarylgroup.

Preferred compounds according to the invention include compounds having the formula II:

(II)

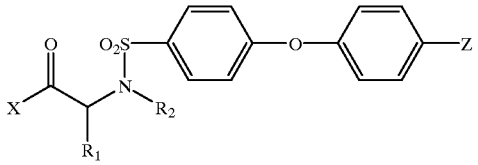

wherein $R_1$, $R_2$ and X are as defined above and Z is a halogen group, an alkyl group, a cycloalkyl group, a heterocycloalkyl group, an O-alkyl group, an S-alkyl group, an aryl group, or a heteroaryl group.

Other preferred compounds include compounds of formula I where Ar is a heteroaryl group containing six ring atoms. More preferably, Ar is pyridyl, pyrimidinyl, pyridazinyl, or pyrazinyl.

Other preferred compounds include those where $R_5$ is H and $R_4$ is an alkyl group. Also preferred are those compounds where $R_5$ is a heteroaryl group and those where $R_5$ is —$CHR_6R_7$, wherein $R_6$ is H or any suitable substituent and $R_7$ is

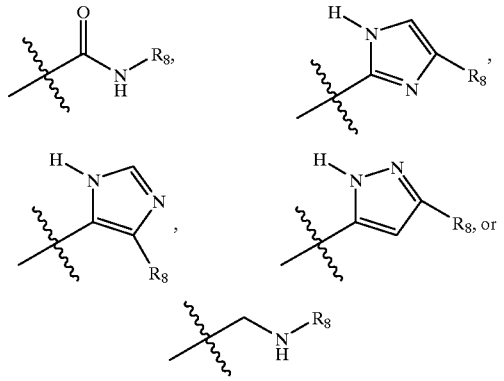

wherein $R_8$ is any suitable substituent.

In the inventive compounds, it is also preferred that $R_4$ is an alkyl group and $R_3$ is an alkyl group, an O-alkyl group, or an S-alkyl group. More preferably, $R_3$ is a —$CH_2CH_2$— heteroaryl group, an —$OCH_2$— heteroaryl group, or an —S—$CH_2$-heteroaryl group.

Other preferred compounds include those where $R_4$ and $R_5$ together form the group —$CH_2CH_2$—.

Inventive compounds of formula I wherein X is NHOH are preferably selected from those possessing inhibitory potencies (Ki's) against human gelatinase A (Gel A), human collagenase-3 (Coll-3), and/or human stromelysin-1 (Strom) of less than 50 nM, and more preferably of less than 5 nM. Still more preferably, compounds of formula I wherein X is NHOH are selected from those possessing Ki's against Gel A and/or Coll-3 of less than 0.2 nM and/or those possessing an inhibition selectivity as defined by the ratio of Ki for human collagenase-1 (HFC) and the Ki for Coll-3, of greater than 50.

Inventive compounds of formula I wherein X is OH are preferably selected from those possessing Ki's against Gel A of less than 1 μM, more preferably less than 200 nM, and still more preferably less than 50 nM. Assays for determining Ki's are described in greater detail infra.

Particularly preferred compounds falling within formula I include:

2(R)-1-[4-(4-Bromophenoxy)benzenesulfonyl]-N-hydroxy-piperidine-2-carboxamide,

2(R)-1-[4-(4-Chlorophenoxy)benzenesulfonyl]-N-hydroxy-piperidine-2-carboxamide,

2(R)-1-[4-(4-Fluorophenoxy)benzenesulfonyl]-N-hydroxy-piperidine-2-carboxamide,

2(R)-1-[4-(4-Methylphenoxy)benzenesulfonyl]-N-hydroxy-piperidine-2-carboxamide,

2(R)-1-[4-(4-Methoxyphenoxy)benzenesulfonyl]-N-hydroxy-piperidine-2-carboxamide, 2(R)-1-[4-Phenoxybenzenesulfonyl]-N-hydroxypiperidine-2-carboxamide, 2(R)-1-[4-(Biphenyl-4-yl)oxybenzenesulfonyl]-N-hydroxy-piperidine-2-carboxamide, 2(R)-1-[4-(4-(Imidazol-1-yl)phenoxy)benzenesulfonyl]-N-hydroxy-piperidine-2-carboxamide, 2(R)-1-[4-(4-(Imidazol-2-yl)phenoxy)benzenesulfonyl]-N-hydroxy-piperidine-2-carboxamide, 2(R)-1-[4-(4-(Imidazol4-yl)phenoxy)benzenesulfonyl]-N-hydroxy-piperidine-2-carboxamide, 2(R)-1-[4-(4-(Pyrazol-4-yl)phenoxy)benzenesulfonyl]-N-hydroxy-piperidine-2-carboxamide, 2(R)-1-[4-(4-(Pyrazol-3-yl)phenoxy)benzenesulfonyl]-N-hydroxy-piperidine-2-carboxamide, 2(R)-1-[4-(4-(2-(Dimethylamino)ethyl)phenoxy)benzenesulfonyl]-N-hydroxypiperidine-2-carboxamide, 2(R)-1-[4-(Pyrid-4-yl)oxybenzenesulfonyl]-N-hydroxypiperidine-2-carboxamide, 2(R), 3(S)-1-[4-(4-Chlorophenoxy)benzenesulfonyl]-N-hydroxy-3-methylpiperidine-2-carboxamide, 2(R), 3(S)-1-[4-(4-Fluorophenoxy)benzenesulfonyl]-N-hydroxy-3-methylpiperidine-2-carboxamide, 2(R), 3(S)-1-[4-(4-Methoxyphenoxy)benzenesulfonyl]-N-hydroxy-3-methylpiperidine-2-carboxamide, 2(R), 3(S)-1-[4-(4-(Imidazol-1-yl)phenoxy)benzenesulfonyl]-N-hydroxy-3-methylpiperidine-2-carboxamide, 2(R), 3(S)-1-[4-(4-(Imidazol-2-yl)phenoxy)benzenesulfonyl]-N-hydroxy-3-methylpiperidine-2-carboxamide, 2(R), 3(S)-1-[4-(4-(Imidazol-4-yl)phenoxy)benzenesulfonyl]-N-hydroxy-3-methylpiperidine-2-carboxamide, 2(R), 3(S)-1-[4-(4-(Pyrazol-4-yl)phenoxy)benzenesulfonyl]-N-hydroxy-3-methylpiperidine-2-carboxamide, 2(R), 3(S)-1-[4-(4-(Pyrazol-3-yl)phenoxy)benzenesulfonyl]-N-hydroxy-3-methylpiperidine-2-carboxamide, 2(R), 3(S)-1-[4-(Pyrid-4-yl)oxybenzenesulfonyl]-N-hydroxy-3-methylpiperidine-2-carboxamide, 2(R)-2-[4-(4-Bromophenoxy)benzenesulfonyl][(pyridin-3-yl)methyl]amino-N-hydroxy-3-methylbutanamide, 2(R)-2-[4-(4-Chlorophenoxy)benzenesulfonyl][(pyridin-3-yl)methyl]amino-N-hydroxy-3-methylbutanamide, 2(R)-2-[4-(4-Chlorophenoxy)benzenesulfonyl][(pyridin-4-yl)methyl]amino-N-hydroxy-3-methylbutanamide, 2(R)-2-[4-(4-Chlorophenoxy)benzenesulfonyl][(imidazol-2-yl)methyl]amino-N-hydroxy-3-methylbutanamide, 2(R)-2-[4-(4-Chlorophenoxy)benzenesulfonyl][2-(imidazol-2-yl)ethyl]amino-N-hydroxy-3-methylbutanamide, 2(R)-2-[4-(4-Chlorophenoxy)benzenesulfonyl][2-(imidazol-4-yl)ethyl]amino-N-hydroxy-3-methylbutanamide, 2(R)-2-[4-(4-Chlorophenoxy)benzenesulfonyl][2-(pyrazol-3-yl)ethyl]amino-N-hydroxy-3-methylbutanamide, 2(R)-2-[4-(4-Chlorophenoxy)benzenesulfonyl][2-(methylcarbamoyl)ethyl]amino-N-hydroxy-3-methylbutanamide, 2(R)-2-[4-(4-Chlorophenoxy)benzenesulfonyl][2-(methylamino)ethyl]amino-N-hydroxy-3-methylbutanamide, 2(R)-2-[4-(4-Chlorophenoxy)benzenesulfonyl][(pyridin-3-yl)methyl]amino-N-hydroxy-2-cyclohexylacetamide, 2(R)-2-[4-(4-Chlorophenoxy)benzenesulfonyl][2-(imidazol-2-yl)ethyl]amino-N-hydroxy-2-cyclohexylacetamide, 2(R)-2-[4-(4-Chlorophenoxy)benzenesulfonyl][2-(methylcarbamoyl)ethyl]amino-N-hydroxy-2-cyclohexylacetamide, 2(R)-2-[4-(4-Chlorophenoxy)benzenesulfonyl][(pyridin-3-yl)methyl]amino-N-hydroxy-2-(tetrahydro-2H-pyran-4-yl)acetamide, 2(R)-2-[4-(4-Chlorophenoxy)benzenesulfonyl][2-(methylcarbamoyl)ethyl]amino-N-hydroxy-2-(tetrahydro-2H-pyran-4-yl)acetamide, 2(R)-2-[4-(4-Chlorophenoxy)benzenesulfonyl][(pyridin-3-yl)methyl]amino-N-hydroxy-2-(1-methylpiperidin-4-yl)acetamide, 2(R)-2-[4-(4-Chlorophenoxy)benzenesulfonyl][(pyridin-3-yl)methyl]amino-N-hydroxy-2-(1-acetylpiperidin-4-yl)acetamide, 2(R)-2-[4-(4-Chlorophenoxy)benzenesulfonyl][(2-(methylcarbamoyl)ethyl]amino-N-hydroxy-2-(1-methylpiperidin-4-yl)acetamide, 2(R), 3(R)-2-[4-(4-Chlorophenoxy)benzenesulfonyl](methyl)amino-N,3-dihydroxybutanamide, 2(R), 3(R)-2-[4-(4-Chlorophenoxy)benzenesulfonyl](methyl)amino-N-hydroxy-3-methoxybutanamide, 2(R), 3(R)-2-[4-(4-Chlorophenoxy)benzenesulfonyl](methyl)amino-N-hydroxy-3-(2-methoxyethoxy)butanamide, 2(R), 3(R), 3(2'(S))-2-[4-(4-Chlorophenoxy)benzenesulfonyl](methyl)amino-N-hydroxy-3-[(5-oxopyrrolidin-2-yl)methoxy]butanamide, 2(R), 3(R)-2-[4-(4-Chlorophenoxy)benzenesulfonyl](methyl)amino-N-hydroxy-3-[(1-methylimidazol-2-yl)methoxy]butanamide, 2(R)-2-(4-(4-Chlorophenoxy)benzenesulfonyl](methyl)amino-N-hydroxy-2-(1-methylpiperidin-4-yl)acetamide, 2(R)-2-[4-(4-Chlorophenoxy)benzenesulfonyl](methyl)amino-N-hydroxy-2-cyclohexylacetamide, 2(R)-2-[4-(4-Chlorophenoxy)benzenesulfonyl](methyl)amino-N-hydroxy-2-(tetrahydro-2H-pyran-4-yl)acetamide, 2(S), 3(R)-2-[4-(4-Chlorophenoxy)benzenesulfonyl](methyl)amino-N-hydroxy-3-[(5-methylisoxazol-3-yl)methylsulfanyl]butanamide, 2(S), 3(R)-2-[4-(4-Chlorophenoxy)benzenesulfonyl](methyl)amino-N-hydroxy-3-[(pyrid-2-yl)methylsulfanyl]butanamide, 2(S), 3(R)-2-[4-(4-Chlorophenoxy)benzenesulfonyl](methyl)amino-N-hydroxy-3-[(1-methylimidazol-2-yl)methylsulfanyl]butanamide, 2(S), 3(R)-2-[4-(4-Chlorophenoxy)benzenesulfonyl](methyl)amino-N-hydroxy-3-[(1-methylpiperidin-4-yl)methylsulfanyl]butanamide, 2(S), 3(R)-2-[4-(4-Chlorophenoxy)benzenesulfonyl](methyl)amino-N-hydroxy-3-[2-(dimethylamino)ethylsulfanyl]butanamide, 2(S)-2-[4-(4-Chlorophenoxy)benzenesulfonyl](methyl)amino-N-hydroxy-3-[(5-methylisoxazol-3-yl)methylsulfanyl]propanamide, 2(S)-2-[4-(4-Chlorophenoxy)benzenesulfonyl](methyl)amino-N-hydroxy-3-[(pyrid-2-yl)methylsulfanyl]propanamide, 2(S)-2-[4-(4-Chlorophenoxy)benzenesulfonyl](methyl)amino-N-hydroxy-3-[(1-methylimidazol-2-yl)methylsulfanyl]propanamide, 2(R), 3(R)-2-[4-(4-Fluorophenoxy)benzenesulfonyl](methyl)amino-N,3-dihydroxybutanamide, 2(R), 3(R)-2-[4-(4-Fluorophenoxy)benzenesulfonyl](methyl)amino-N-hydroxy-3-methoxybutanamide, 2(R), 3(R)-2-[4-(4-Fluorophenoxy)benzenesulfonyl](methyl)amino-N-hydroxy-3-(2-methoxyethoxy)butanamide, 2(R), 3(R), 3(2'(S))-2-[4-(4-Fluorophenoxy)benzenesulfonyl](methyl)amino-N-hydroxy-3-[(5-oxopyrrolidin-2-yi)methoxy]butanamide, 2(R), 3(R)-2-[4-(4-Fluorophenoxy)benzenesulfonyl](methyl)amino-N-hydroxy-3-[(1-methylimidazol-2-yl)methoxy]butanamide, 2(R)-2-[4-(4-Fluorophenoxy)benzenesulfonyl](methyl)amino-N-hydroxy-2-(1-methylpiperidin4-yl)acetamide, 2(R)-2-[4-(4-Fluorophenoxy)benzenesulfonyl](methyl)amino-N-hydroxy-3-methylbutanamide, 2(R)-2-[4-(4-Fluorophenoxy)benzenesulfonyl](methyl)amino-N-hydroxy-2-cyclohexylacetamide, 2(R)-2-[4-(4-Fluorophenoxy)benzenesulfonyl](methyl)amino-N-hydroxy-2-(tetrahydro-2H-pyran-4-yl)acetamide, 2(S), 3(R)-2-[4-(4-Fluorophenoxy)benzenesulfonyl](methyl)amino-N-hydroxy-3-[(5-methylisoxazol-3-yl)methylsulfanyl]butanamide, 2(S), 3(R)-2-[4-(4-Fluorophenoxy)benzenesulfonyl](methyl)amino-N-hydroxy-3-[(pyrid-2-yl)methylsulfanyl]butanamide, 2(S), 3(R)-2-[4-(4-Fluorophenoxy)benzenesulfonyl](methyl)amino-N-hydroxy-3-[(1-methylimidazol-2-yl)methylsulfanyl]butanamide, 2(S), 3(R)-2-[4-(4-Fluorophenoxy)benzenesulfonyl](methyl)amino-N-hydroxy-3-[(1-methylpiperidin-4-yl)methylsulfanyl]butanamide, 2(S), 3(R)-2-[4-(4-Fluorophenoxy)benzenesulfonyl](methyl)amino-N-hydroxy-3-[2-(dimethylamino)ethylsulfanyl]butanamide, 2(S)-2-[4-(4-Fluorophenoxy)benzenesulfonyl](methyl)amino-N-hydroxy-3-[(5-methylisoxazol-3-yl)methylsulfanyl]propanamide, 2(S)-2-[4-(4-Fluorophenoxy)benzenesulfonyl](methyl)amino-N-hydroxy-3-[(pyrid-2-yl)methylsulfanyl]propanamide, 2(S)-2-[4-(4-Fluorophenoxy)benzenesulfonyl](methyl)amino-N-hydroxy-3-[(1-methylimidazol-2-yl)methylsulfanyl]propanamide, 2(R), 3(R)-2-[4-(Pyrid-4-yl)oxybenzenesulfonyl](methyl)amino-N,3-dihydroxybutanamide, 2(R), 3(R)-2-[4-(Pyrid-4-yl)oxybenzenesulfonyl](methyl)amino-N-hydroxy-3-methoxybutanamide, 2(R), 3(R)-2-[4-(Pyrid-4-yl)oxybenzenesulfonyl](methyl)amino-N-hydroxy-3-(2-methoxyethoxy)butanamide, 2(R), 3(R), 3(2'(S))-2-[4-(Pyrid-4-yl)oxybenzenesulfonyl](methyl)amino-N-hydroxy-3-[(5-oxopyrrolidin-2-yl)methoxy]butanamide, 2(R)-2-[4-(Pyrid-4-yl)oxybenzenesulfonyl](methyl)amino-N-hydroxy-3-methylbutanamide, 2(R)-2-[4-(Pyrid-4-yl)oxybenzenesulfonyl](methyl)amino-N-hydroxy-2-cyclohexylacetamide, 2(R)-2-[4-(Pyrid-4-yl)oxybenzenesulfonyl](methyl)amino-N-hydroxy-2-cyclopentylacetamide, 2(R)-2-[4-(Pyrid-4-yl)oxybenzenesulfonyl](methyl)amino-N-hydroxy-2-cyclopropylacetamide, 2(R)-2-[4-(Pyrid-4-yl)oxybenzenesulfonyl](methyl)amino-N-hydroxy-2-(tetrahydro-2H-pyran-4-yl)acetamide, 2(S), 3(R)-2-[4-(Pyrid-4-yl)oxybenzenesulfonyl](methyl)amino-N-hydroxy-3-[(5-methylisoxazol-3-yl)methylsulfanyl]butanamide, 2(S)-2-[4-(Pyrid-4-yl)oxybenzenesulfonyl](methyl)amino-N-hydroxy-3-[(5-(hydroxymethyl)isoxazol-3-yl)methylsulfanyl]propanamide, 2(S)-2-[4-(Pyrid-4-yl)oxybenzenesulfonyl](methyl)amino-N-hydroxy-3-[(phenyl)methylsulfanyl]propanamide, 2(S)-2-[4-(Pyrid-4-yl)oxybenzenesulfonyl](methyl)amino-N-hydroxy-3-[(4-fluorophenyl)methylsulfanyl]propanamide, 2(S)-2-[4-(Pyrid-4-yl)oxybenzenesulfonyl](methyl)amino-N-hydroxy-3-[(1-methylimidazol-2-yl)methylsulfanyl]propanamide, 2(R)-2-[4-(4-Bromophenoxy)benzenesulfonyl](methyl)amino-N-hydroxy-3-methylbutanamide, 2(R)-2-[4-(4-Chlorophenoxy)benzenesulfonyl](methyl)amino-N-hydroxy-3-methylbutanamide, 2(R)-2-[4-(4-Fluorophenoxy)benzenesulfonyl](methyl)amino-N-hydroxy-3-methylbutanamide, 2(R)-2-[4-(4-Methylphenoxy)benzenesulfonyl](methyl)amino-N-hydroxy-3-methylbutanamide, 2(R)-2-[4-(4-Methoxyphenoxy)benzenesulfonyl](methyl)amino-N-hydroxy-3-methylbutanamide, 2(R)-2-[4-Phenoxybenzenesulfonyl](methyl)amino-N-hydroxy-3-methylbutanamide, 2(R)-2-[4-(Biphenyl-4-yl)oxybenzenesulfonyl]-N-hydroxy-piperidine-2-carboxamide, 2(R)-2-[4-(4-(Imidazol-1-yl)phenoxy)benzenesulfonyl](methyl)amino-N-hydroxy-3-methylbutanamide, 2(R)-2-[4-(4-(Imidazol-2-yl)phenoxy)benzenesulfonyl](methyl)amino-N-hydroxy-3-methylbutanamide, 2(R)-2-[4-(4-(Imidazol4-yl)phenoxy)benzenesulfonyl](methyl)amino-N-hydroxy-3-methylbutanamide, and 2(R)-2-[4-(4-(2-(dimethylamino)ethyl)phenoxy)benzenesulfonyl](methyl)amino-N-hydroxy-3-methylbutanamide, 2(R)-1-[4-(4-Bromophenoxy)benzenesulfonyl]-N-hydroxy-hexahydro-1H-azepine-2-carboxamide, 2(R)-1-[4-(4-Chlorophenoxy)benzenesulfonyl]-N-hydroxy-hexahydro-1H-azepine-2-carboxamide, 2(R)-1-[4-(4-Fluorophenoxy)benzenesulfonyl]-N-hydroxy-hexahydro-1H-azepine-2-carboxamide, 2(R)-1-[4-(4-Methylphenoxy)benzenesulfonyl]-N-hydroxy-hexahydro-1H-azepine-2-carboxamide, 2(R)-1-[4-(4-Methoxyphenoxy)benzenesulfonyl]-N-hydroxy-hexahydro-1H-azepine-2-carboxamide, 2(R)-1-[4-Phenoxybenzenesulfonyl]-N-hydroxy-hexahydro-1H-azepine-2-carboxamide, 2(R)-1-[4-(Biphenyl-4-yl)oxybenzenesulfonyl]-N-hydroxy-hexahydro-1H-azepine-2-carboxamide, 2(R)-1-[4-(4-(Imidazol-1-yl)phenoxy)benzenesulfonyl]-N-hydroxy-piperidine-2-carboxamide, 2(R)-1-[4-(4-(Imidazol-2-yl)phenoxy)benzenesulfonyl]-N-hydroxy-hexahydro-1H-azepine-2-carboxamide, 2(R)-1-[4-(4-(Imidazol-4-yl)phenoxy)benzenesulfonyl]-N-hydroxy-hexahydro-1H-azepine-2-carboxamide, 2(R)-1-[4-(4-(Pyrazol-4-yl)phenoxy)benzenesulfonyl]-N-hydroxy-hexahydro-1H-azepine-2-carboxamide, 2(R)-1-[4-(4-(Pyrazol-3-yl)phenoxy)benzenesulfonyl]-N-hydroxy-hexahydro-1H-azepine-2-carboxamide, 2(R)-1-[4-(4-(2-(Dimethylamino)ethyl)phenoxy)benzenesulfonyl]-N-hydroxy-hexahydro-1H-azepine-2-carboxamide, 2(R)-1-[4-(Pyrid-4-yl)oxybenzenesulfonyl]-N-hydroxy-hexahydro-1H-azepine-2-carboxamide, 2(R), 3(S)-1-[4-(4-Chlorophenoxy)benzenesulfonyl]-N-hydroxy-3-methyl-hexahydro-1H-azepine-2-carboxamide, 2(R), 3(S)-1-[4-(4-Fluorophenoxy)benzenesulfonyl]-N-hydroxy-3-methyl-hexahydro-1H-azepine-2-carboxamide, 2(R), 3(S)-1-[4-(4-Methoxyphenoxy)benzenesulfonyl]-N-hydroxy-3-methyl-hexahydro-1H-azepine-2-carboxamide, 2(R), 3(S)-1-[4-(4-(Imidazol-1-yl)phenoxy)benzenesulfonyl]-N-hydroxy-3-methyl-hexahydro-1H-azepine-2-carboxamide, 2(R), 3(S)-1-[4-(4-(Imidazol-2-yl)phenoxy)benzenesulfonyl]-N-hydroxy-3-methyl-hexahydro-1H-azepine-2-carboxamide, 2(R), 3(S)-1-[4-(4-(Imidazol-4-yl)phenoxy)benzenesulfonyl]-N-hydroxy-3-methyl-hexahydro-1H-azepine-2-carboxamide, 2(R), 3(S)-1-[4-(4-(Pyrazol-4-yl)phenoxy)benzenesulfonyl]-N-hydroxy-3-methyl-hexahydro-1H-azepine-2-carboxamide, 2(R), 3(S)-1-[4-(4-(Pyrazol-3-yl)phenoxy)benzenesulfonyl]-N-hydroxy-3-methyl-hexahydro-1H-azepine-2-carboxamide, 2(R), 3(S)-1-[4-(Pyrid-4-yl)oxybenzenesulfonyl]-N-hydroxy-3-methyl-hexahydro-1H-azepine-2-carboxamide, and pharmaceutically acceptable prodrugs, salts, and solvates thereof.

The present invention is further directed to methods of inhibiting metalloproteinase activity, for example in mammalian tissue, by administering a compound of formula I, or a pharmaceutically acceptable prodrug, salt, or solvate thereof. The activity of the inventive compounds as inhibitors of metalloproteinases, such as MMPs (including stromelysins, collagenases, gelatinases, and/or matrilysin) and/or TNF- convertase, may be measured by any of the methods available to those skilled in the art, including in vivo and/or in vitro assays. Examples of suitable assays for activity measurements include those described in *Anal. Biochem.*, vol. 147, p. 437 (1985); *Anal Biochem.*, vol. 180, p. 110 (1989); *FEBS,* vol. 96, p. 263 (1992); and European Patent Application No. 0 606 046, the disclosures of which are incorporated herein by reference.

Administration of the compounds of formula I, or their pharmaceutically acceptable prodrugs, salts, or solvates, may be performed according to any of the accepted modes of administration available to those skilled in the art. Illustrative examples of suitable modes of administration include oral, nasal, parenteral, topical, transdermal, and rectal. Preferably, the mode of administration is oral.

The inventive compounds of formula I, or their pharmaceutically acceptable prodrugs, salts, or solvates, may be administered as a pharmaceutical composition in any suitable pharmaceutical form recognizable to the skilled artisan. Suitable pharmaceutical forms include, but are not limited to, solid, semisolid, liquid, or lyophilized formulations, such as tablets, powders, capsules, suppositories, suspensions, and aerosols. Preferably, the pharmaceutical form is a tablet or capsule for oral administration. The pharmaceutical composition may also include suitable excipients, diluents, vehicles, and carriers, as well as other pharmaceutically active agents, depending upon the intended use.

Acceptable methods of preparing suitable pharmaceutical forms of the pharmaceutical compositions are known to those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration. Illustrative examples of such methods include those described in *Remington's Pharmaceutical Sciences,* 18th edition (1990).

Solid or liquid pharmaceutically acceptable carriers, diluents, vehicles, or excipients may be employed in the pharmaceutical compositions. Illustrative solid carriers include starch, lactose, calcium sulphate dihydrate, terra alba, sucrose, talc, gelatin, agar, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g. solution), or a nonaqueous or aqueous liquid suspension.

A dose of the pharmaceutical composition contains at least a therapeutically effective amount of the active compound (i.e., a compound of the formula I, or a pharmaceutically acceptable prodrug, salt, or solvate thereof), and preferably is made up of one or more pharmaceutical dosage units. An exemplary dosage unit for a mammalian host contains an amount of from 0.1 milligram up to 500 milligrams of active compound per kilogram body weight of the host, preferably 0.1 to 200 milligrams, more preferably 50 milligrams or less, and even more preferably about 10 milligrams or less, per kilogram of the host weight. The selected dose may be administered to a mammal, for example, a human patient in need of treatment mediated by inhibition of metalloproteinase activity, by any known method of administrating the dose including: topically, for example, as an ointment or cream; orally; rectally, for example, as a suppository; parenterally by injection; or continuously by intravaginal, intranasal, intrabronchial, intraaural, or intraocular infusion.

The amount of the inventive compounds, salts, solvates, and/or prodrugs to be administered will vary based upon a number of factors, including the specific metalloproteinase to be inhibited, the degree of inhibition desired, the characteristics of the mammalian tissue in which inhibition is desired, the metabolic stability and activity of the particular inventive compound employed, and the mode of administration. One skilled in the art may readily determine a suitable dosage according to methods known to the art. Preferably, the amount of inventive compound of formula I, or their pharmaceutically acceptable prodrugs, salts, or solvates, administered ranges from 0.1 mg/kg body weight to 100 mg/kg body weight per day.

The inventive compounds, and the salts, solvates, and prodrugs thereof, may be prepared by employing the techniques available in the art using starting materials that are readily available. Exemplary methods of preparing the inventive compounds are described below. In the following schemes, unless otherwise indicated, $R_1$, $R_2$, and Ar are as defined above.

hexafluorophosphate, or propanephosphonic anhydride in an inert polar solvent, such as dimethylformamide. Alternatively, compounds of formula III can be reacted with hydroxylamine in a suitable solvent mixture, such as THF/t-butanol/dichloromethane or water/dichloromethane, preferably at 0° C., to give hydroxamic acids of formula I. Compounds of formula III are generally prepared, in a form directly useful for further reaction without isolation, by allowing carboxylic acids of formula Ib to react with thionyl chloride or oxalyl chloride, preferably in the presence of a catalytic amount of dimethylformamide, in dichoromethane solvent at −78° C. to room temperature.

Alternatively, the coupling reactions described above may be carried out with compounds of formula Ib (or III) and O-protected derivatives of hydroxylamine (where Pg is a Scheme 1

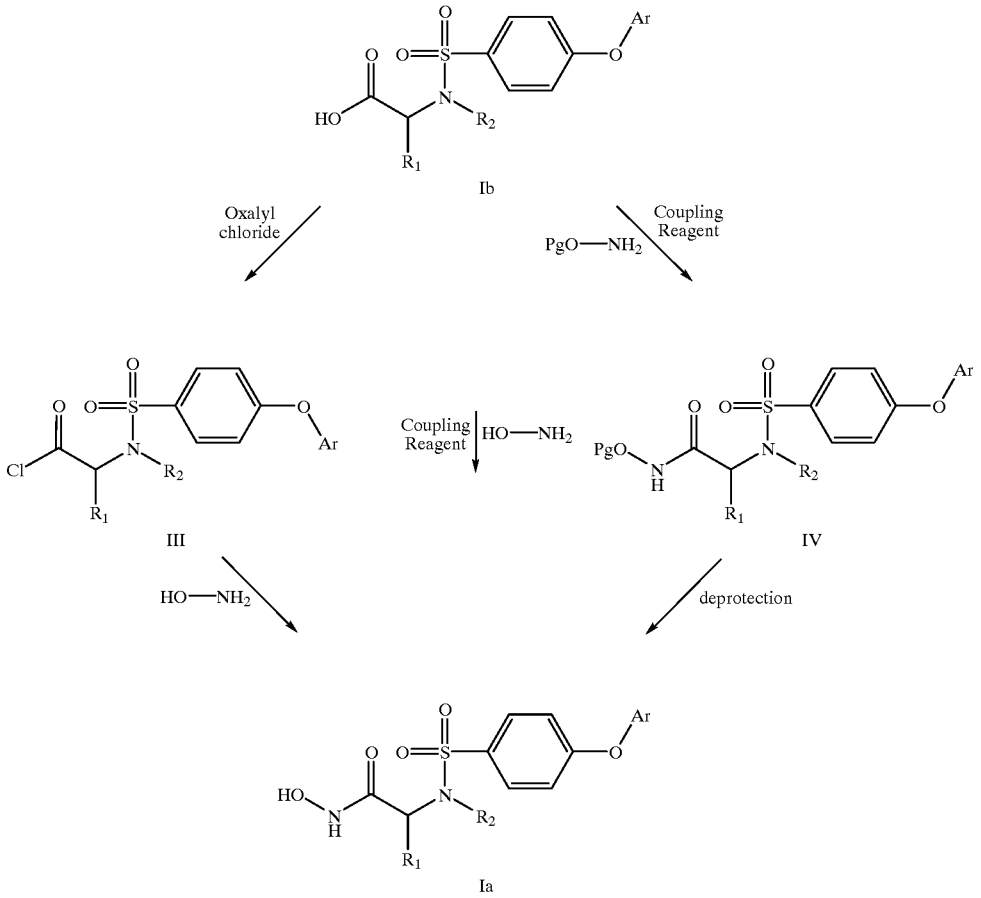

As illustrated in Scheme 1, hydroxamic acids of formula Ia (compounds of formula I where X is —NH—OH) can be prepared by reacting the corresponding carboxylic acids of formula Ib (compounds of formula I where X is —OH) with hydroxylamine in the presence of a suitable peptide coupling reagent, for example, 1,1'-carbonyldimidazole, N-(dimethylaminopropyl)-N'-ethyl carbodiimide, benzotriazol-1-yloxy-tris(dimethylamino)phosphonium suitable protecting group, such as benzyl, tert-butyl, t-butyldimethylsilyl, or t-butyidiphenylsilyl) to give compounds of formula IV. Deprotection of compounds of formula IV using conventional methods (for example, see "Protective Groups in Organic Synthesis", T. W. Greene and P. G. M. Wuts, Wiley-Interscience 1991, the disclosure of which is incorporated herein by reference) provides compounds of formula Ia.

Scheme 2

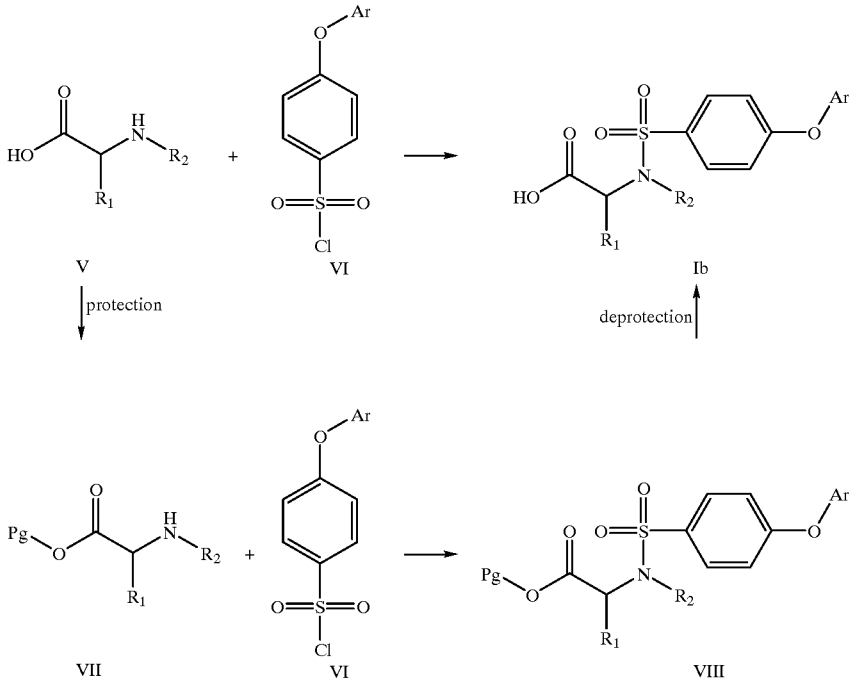

As shown in Scheme 2, carboxylic acids of formula Ib can be prepared by reacting N-substituted-α-amino acids of formula V with arylsulfonyl chlorides of formula VI, under biphasic basic conditions as described, for example, in "The Chemistry of the Amino Acids", J. P. Greenstein and M. Winitz, Robert E. Krieger Publishing Company, 1984, p. 886–889, the disclosure of which is incorporated herein by reference.

Alternatively, carboxylic acids Ib can be prepared by reacting N-substituted-α-amino acid derivatives VII, where Pg is any suitable protecting group as described, for example, in "Protective Groups in Organic Synthesis", T. W. Greene and P. G. M. Wuts, Wiley-Interscience 1991 (the disclosure of which is incorporated herein by reference), with aryl sulfonyl chlorides VI to give sulfonamides VIII under any of a variety of reaction conditions that have been reported in the literature for the sulfonylation of amino acid derivatives (see, for example, "The Chemistry of the Amino Acids", J. P. Greenstein and M. Winitz, Robert E. Krieger Publishing Company, 1984, p. 886–889). Deprotection of VIII to give the acids Ib can be carried out as appropriate to the protecting group Pg. As is evident to those skilled in the art, manipulations of functionality in the groups $R_1$, $R_2$, and/or Ar may be readily effected at the stage of VII prior to the deprotection of VIII to Ib. Amino acids V are commercially-available, or can be prepared according to methods familiar to those skilled in the art.

Scheme 3

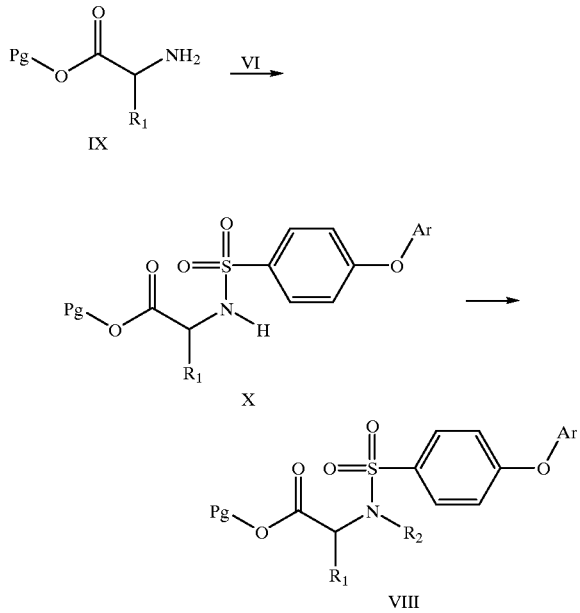

In cases where the N-substituted α-amino acid of formula V is not readily available, the sequence shown in Scheme 3 can be employed to prepare compounds of formula VIII. In this case, protected α-amino acids of formula IX are sulfonylated as described above to provide sulfonamides of formula X. Treatment of X with an alkylating agent $R_2$-X in the presence of a suitable base, such as potassium carbonate or sodium hydride, in a aprotic solvent, such as N,N-dimethylformamide, at 0° C. to 60° C., preferably at 25° C., for 1 to 24 h provides compounds of formula VIII.

Scheme 4

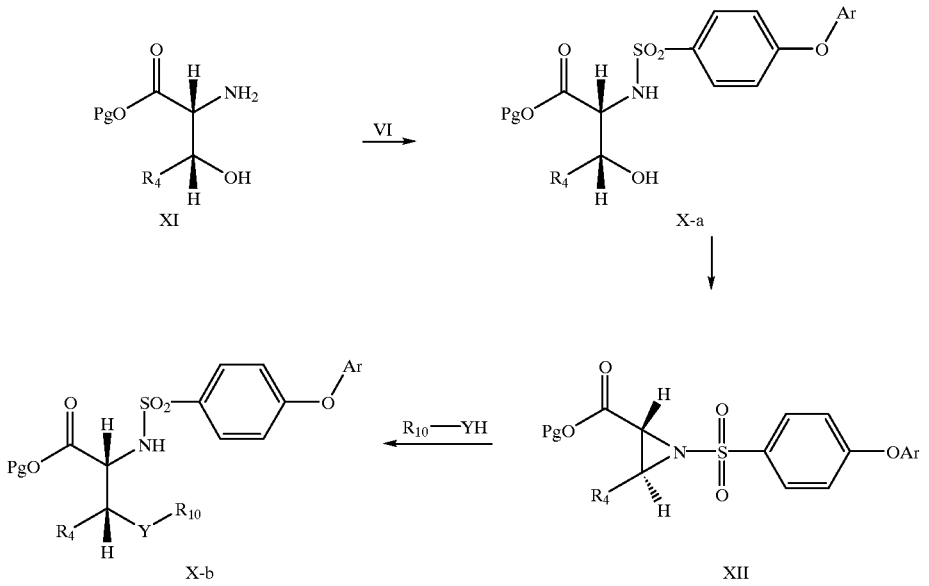

In some cases, elaboration of the $R_1$ group in compounds of formula X is advantageous; one such sequence is outlined in Scheme 4, above. In Scheme 4, $R_{10}$ is hydrogen, an alkyl group, a cycloalkyl group, a heterocycloalkyl group, an aryl group, or a heteroaryl group, and Y is oxygen or sulfur. The reaction scheme proceeds as follows. Sulfonylation of D-α-amino-β-hydroxy amino esters of formula XI (e.g., esters of D-serine when $R_4$ is H, and esters of D-allo-threonine when $R_4$ is Me) with sulfonyl chlorides of formula VI as described above provides compounds of formula X-a. Treatment of sulfonamides of formula X-a with diethyl azodicarboxylate and triphenylphosphine in a suitable inert solvent, such as tetrahydrofuran, at 0° C. to 50° C. for 1 to 24 h provides sulfonyl aziridines of formula XII. Treatment of aziridines XII with alcohols $R_{10}$—OH (i.e., where $R_3$ is —$OR_{10}$) or thiols $R_{10}$—SH (i.e., where $R_3$ is —$SR_{10}$) in the presence of a suitable acid catalyst, such as boron trifluoride etherate, in an inert solvent such as dichloromethane or 1,2-dichloroethane, for 0.5 to 48 h at 0° C. to 60° C., preferably at 25° C. provides compounds of formula X-b.

Scheme 5

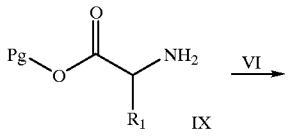

-continued

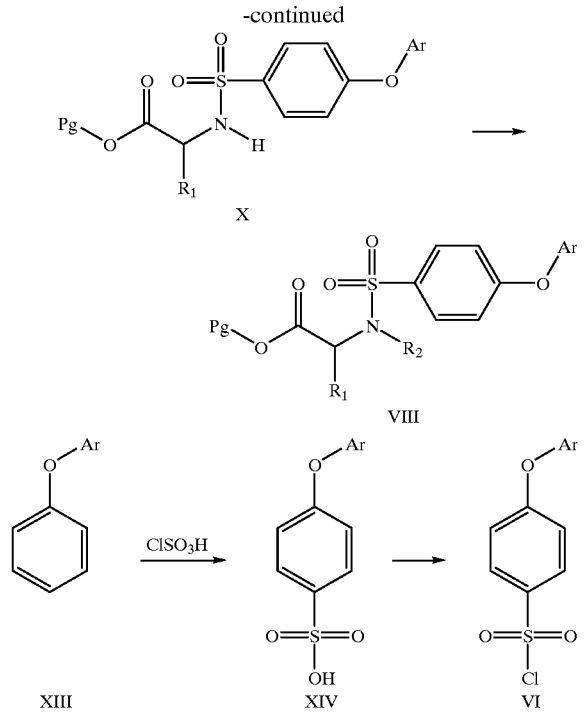

Aryl sulfonyl chlorides VI are most readily available by chlorosulfonylation of the corresponding aryl phenyl ethers XIII, as outlined in Scheme 5 above. In general, treatment of XIII with a little over one molar equivalent of chlorosulfonic acid in a suitable inert solvent, such as 1,2-dichloroethane or dichloromethane, at −20° C. to 25° C. for a period of one to twenty-four hours generates the corresponding sulfonic acid intermediate XIV. Without isolation, XIV can be further converted to the sulfonyl chloride VI by reaction with a chlorinating agent, such as oxalyl chloride or thionyl chloride, and optionally cataltyic DMF. In some cases, excess chlorosulfonic acid is effective at converting XIII directly to VI via the intermediacy of XIV. Compounds of the formula XIII are commercially-available or may be readily prepared by those skilled in the art from commercially-available materials by the Ullman reaction.

Other compounds of formula I may be prepared by methods known to those skilled in the art in a manner analogous to the general procedures described above. Specific examples of methods used to prepare the inventive compounds are described below along with illustrative preferred embodiments of the inventive compounds of formula I, or their pharmaceutically acceptable prodrugs, salts, or solvates.

The following specific examples are intended to be illustrative of the invention and should not be construed as limiting the scope of the invention as defined by the appended claims. These examples include preferred embodiments of the inventive compounds.

EXAMPLES

Example 1

Preparation of Intermediate Compounds of Formula VIII-a

VIII-a

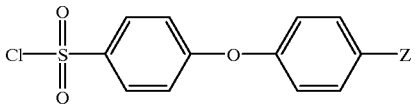

Example 1 (a) 4-Phenoxybenzenesulfonyl chloride {VIII-a: Z=H}

To a stirred solution of 42.5 g (0.25 mol) of phenyl ether in 200 mL of dichloromethane at −20° C. under argon was slowly added 23.3 g (0.20 mol) of chlorosulfonic acid. After the addition was complete, the reaction was allowed to slowly warm to room temperature. After 16 h, 150 mL of isooctane was added, and the solution was concentrated to an oily residue. Redissolution in 200 mL of 1:3 dichloromethane/isooctane and reconcentration with cooling to about 100 mL gave a solid. The supernatant was decanted, and the solid triturated with additional isooctane and then dried in vacuo to give 55.2 g of crude 4-phenoxybenzene sulfonic acid. The crude acid was dissolved in 200 mL of dichloromethane, and 22 mL (32 g, 0.25 mol) of oxalyl chloride was added, followed by 2.5 mL of N,N-dimethylformamide. After 2 days, the reaction solution was poured into 200 mL of ice water, and extracted with 400 mL of hexane. The organic layer was washed with 100 mL of water and 100 mL of brine, dried over magnesium sulfate, and concentrated. Recrystallization of the residue from dichloromethane/isooctane gave 38.5 g of 4-phenoxybenzenesulfonyl chloride as a white solid: mp 41.5° C.; $^1$H-NMR ($CDCl_3$) δ 7.10 (apparent T, 4 H, J=7 Hz), 7.28 (t, 1H, J=7 Hz), 7.46 (t, 2H, J=8 Hz), 7.98 (d, 2H, J=8.8 Hz).

Example 1 (b) 4-(4-Methylphenoxy)benzenesulfonyl chloride {VIII-a: Z=$CH_3$}

To a solution of 1.84 g (10.0 mmol) of 4-methyldiphenyl ether (*J. Chem. Soc., Perkin Trans.* 1; 1992, 407–408, which article is entirely incorporated herein by reference) with 2 mL of dichloromethane in an ice-bath was added a solution of chlorosulfonic acid (0.73 mL, 11.0 mmol) in 2 mL of dichloromethane dropwise. The resulting mixture was stirred at 0° C. to room temperature for 2 hr, and then oxalyl chloride (11.14 mL, 13.0 mmol) was added dropwise, followed by 0.15 mL of DMF. The resulting mixture was heated to 40° C. for 1 hr and then allowed to cool to room temperature over a 2 hr period. The reaction mixture was poured into ice-pH 7 phosphate buffer (50 mL), then extracted with ethyl acetate:Hexane (4:3) (3×150 mL). The combined organic layers were washed with brine (75 mL). The aqueous layer was extracted with ethyl acetate/Hexane (4:3) (150 mL). The organic layer was dried over $Na_2SO_4$, then evaporated by vacuum to give crude product as white solid. This solid was triturated with hexane and collected by filtration, then dried under high vacuum to give 1.555 g (57%) of 4-(4-methylphenoxy)benzenesulfonyl chloride as white solid: mp 295–300° C. $^1$H-NMR (dMSO-d6) δ 2.34 (s, 3H), 6.91–6.99 (dd, J=7.7,8.4 Hz, 4H), 7.24–7.27 (d, J=8.4 Hz, 2H), 7.61–7.63 (d, J=8.1 Hz, 2H).

Anal. calc. for $C_{13}H_{11}O_3SCl$: C, 55.22; H, 3.92; S, 11.34; Cl, 12.71. Found: C, 55.06; H, 3.95; S, 11.28; Cl, 12.71.

The following compounds were prepared in a similar fashion:

Example 1 (c) 4-(4-Bromophenoxy)benzenesulfonyl chloride {VIII-a: Z=Br}

From 4-bromobiphenyl ether (supplier: Aldrich): mp 81° C.

Example 1 (d) 4-(4-Chlorophenoxy)benzenesulfonyl chloride {VIII-a: Z=Cl}

From 4-chlorobiphenyl ether (supplier: Transworld): mp 61° C.

Example 1 (e) 4-(4-Fluorophenoxy)benzenesulfonyl chloride {VIII-a: Z=F}

From 4-fluorobiphenyl ether (supplier: Riedel-de Haen): mp 76° C.

Example 1 (f) 4-(4-Iodophenoxy)benzenesulfonyl chloride {VIII-a: Z=I}

From 4-iodobiphenyl ether (supplier: Transworld): mp 85–88° C.

Example 1 (g) 4-(4-Cyanophenoxy)benzenesulfonyl chloride {VIII-a: Z=CN}

From 4-cyanobiphenyl ether (supplier: Transworld): mp 98–102° C.

Example 1 (h) 4-(4-Trifluoromethyphenoxy) benzenesulfonyl chloride {VIII-a: Z=$CF_3$}

From 4-trifluoromethylbiphenyl ether (*J. Chem. Soc., Perkin Trans.* 1 1988, 3229–3232, which article is entirely incorporated herein by reference) mp 265–270° C.; $^1$H-NMR ($CDCl_3$) δ 7.04 (d, J=8.4 Hz, 2H), 7.14 (d, J=8.7 Hz, 2H), 7.65 (d, J=8.8 Hz, 2H), 7.73 (d, J=8.7 Hz, 2H).

Anal. calc. for $C_{13}H_8O_3S_1F_3Cl$ (336.71): C, 46.34; H, 2.39; S, 9.52. Found: C, 46.34; H, 2.49; S, 9.37.

Example 1 (i) 4-(Pyrid-2-yl)oxybenzenesulfonyl chloride

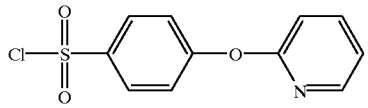

From 2-phenoxypyridine (supplier: ICN): $^1$H-NMR ($CDCl_3$) δ 8.25 (m, 1H), 8.05 (d, 2H, J=9 Hz), 7.81 (t, 1H, J=8 Hz), 7.34 (d, 2H, J=9 Hz), 7.15 (dd, 1H, J=7 & 5 Hz), 7.06 (d, 1H, J=8 Hz).

Example 2

Preparation of Intermediate 4-(Pyridin-4-yl) oxybenzenesulfonyl Chloride Hydrochloride

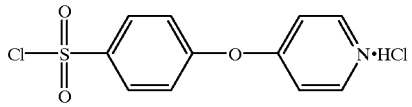

To a suspension of 4-(pyridin-4-yl)oxybenzenesulfonic acid (1.3 kg) in acetonitrile (8 L), was added N,N-dimethylformamide (12.35 mL), and the viscous reaction mixture was heated to 75° C. Thionyl chloride (756 mL) was added to the reaction mixture over 30 minutes. The reaction mixture slowly became less viscous and became homogeneous after 45 minutes, which indicated the reaction was complete. A portion of the solvent (4 L) was evaporated under vacuum and tert-butyl methyl ether (4 L) was added. The resulting slurry was filtered under inert atmosphere. The filter cake was rinsed with tert-butyl methyl ether (2 L), and the solid dried under vacuum to yield 4-(pyridin-4-yl) oxybenzenesulfonyl chloride hydrochloride (1.35 kg) as a hygroscopic, off-white solid of pearlescent flakes: mp 182° C.; $^1$H NMR ($CDCl_3$): δ 8.87 (d, J=7 Hz, 2H), 8.24 (d, J=8.5 Hz, 2H), 7.50 (d, J=8.5 Hz, 2H), 7.43 (d, J=7 Hz, 2H).

The starting material was prepared as follows:

To a vigorously stirred solution of 4-phenoxypyridine (1 kg) in dry 1,2-dichloroethane (3 L) at −10° C. under a stream of argon, chlorosulfonic acid (974 mL) was added slowly. The addition rate of the chlorosulfonic acid was adjusted to keep the reaction temperature below 0° C. After half of the chlorosulfonic acid was added, the exotherm stopped. The cooling bath was removed, and the addition of chlorosulfonic acid continued over 3 hours while the reaction solution warmed to room temperature. While continually purging with inert gas, the vigorously stirred reaction mixture was heated to 45° C. By thin layer chromatography analysis, no more starting material remained after 20 hours.

The reaction mixture was cooled to room temperature and slowly poured into ice cold water (5 L) while stirring. Potassium phosphate tribasic (212 g) was added as a solid to the mixture, and this was stirred for 10 minutes followed by addition of sodium hydroxide (2M) to pH 2. After stirring for 1 hour, the pH was changed to 7 by the addition of sodium hydroxide (2M). Agitation was continued for 5 minutes, and then the organic layer was drained off and discarded. The mixture was extracted a second time with dichloromethane (2L), the mixture agitated for 5 minutes, and the organic layer drained off and discarded. The remaining aqueous mixture was extracted by addition of dichloromethane (6 L), tetrabutylammonium bromide (940 g), and sodium hydroxide (2M) to pH 7. The mixture was agitated for 5 minutes and the organic layer (bottom) drained into a flask. The extraction procedure was repeated twice. The combined organic was dried over magnesium sulfate, filtered, and the solution was concentrated under vacuum to an oil. The residual oil was diluted with 20% ethanol in ethyl acetate (8 L, dry), and hydrogen chloride gas added to a pH of 1. The solid was filtered off and the filter cake rinsed with 20% ethanol in ethyl acetate (2 L). The solid was dried under vacuum at 45° C. for 15 hours to yield 4-[(pyrid-4-yl)oxy] benzenesulfonic acid(1.3 kg) as a white powdery solid.

mp dec. >275 ° C.; $^1$H NMR (300 MHZ, DMSO-$d_6$): δ 8.86 (dd, J=1.5, 7.4 Hz, 2H), 7.84 (dd, J=1.5, 7 Hz, 2H)7.54 (dd, J=1.5, 7.4 Hz, 2H), 7.35 (dd, J=1.5, 7 Hz, 2H). 'Anal. calc. for $C_{11}H_9NO_4S$: C, 52.58; H, 3.61; N, 5.57; S, 12.76. Found: C, 52.50; H, 3.69; N, 5.51; S, 12.67.

Example 3

Preparation of Compounds of Formula I

Example 3(a). 2(R)-2-[4-(4-Bromophenoxy) benzenesulfonyl][(pyridin-3-yl)methyl]amino-N-hydroxy-3-methylbutanamide

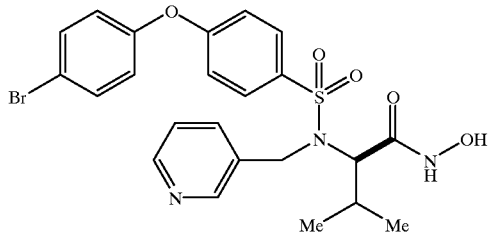

Dry hydrogen chloride was bubbled through a −20° C. solution of 2(R)-N-(tert-butoxy)-2-[4-(4-bromophenoxy) benzenesulfonyl][(pyridin-3-yl)methyl]amino-3-methylbutanamide (750 mg, 1.27 mol) in 20 mL of dichloromethane for 10 min, and the reaction was sealed and stirred at room temperature overnight. The reaction was vented, nitrogen was bubbled through the solution for 20 min, and the solution was concentrated to give, after trituration with ether, 689 mg (79%) of 2(R)-2-[4-(4-bromophenoxy)benzenesulfonyl][(pyridin-3-yl)methyl] amino-N-hydroxy-3-methylbutanamide as a white solid: mp 142.3–143.7° C.; El MS m/e 533 ($M^+$)

Anal. Calcd. for $C_{23}H_{24}BrN_3O_5S$•HCl: C, 48.39; H, 4.41; N, 7.36. Found: C, 48.03; H,4.46; N,7.51.

The starting material was prepared as follows:

(i) Preparation of N-[4-(4-bromophenoxy)benzenesulfonyl]-D-valine t-butyl ester

To a 0° C. suspension of 4-(4-bromophenoxy)benzene sulfonyl chloride (1.10 g, 3.16 mmol) in 20 mL of dichloromethane was added a solution of diisoproylethylamine (1.10 mL, 6.3 mmol) and D-valine tert-butyl ester (660 mg, 3.8 mol) in 11 mL of dichloromethane. The ice bath was removed, and the reaction was stirred for 3 h, diluted with 30 mL dichloromethane, and 30 ml of 1 M HCl was added. The layers were separated, and the aqueous layer was washed with 30 mL of dichloromethane. The combined dichloromethane fractions were washed with brine, dried over $MgSO_4$, and concentrated. The residue was chromatographed on silica, eluting with 25% ethyl acetate in hexane, to give 980 mg (64%) of N-[4-(4-bromophenoxy) benzenesulfonyl]-D-valine t-butyl ester as a white foam.

(ii) Preparation of N-[4-(4-bromophenoxy) benzenesulfonyl]-N-(pyridin-3-yl)methyl-D-valine t-butyl ester To a solution of N-[4-(4-bromophenoxy) benzenesulfonyl]-D-valine t-butyl ester (980 mg, 2.0 mol) in 5 mL of DMF was added potassium carbonate (1.53 g, 11.1 mol), 3-picolyl chloride hydrochloride (414 mg, 2.53 mol), and Kl (67 mg, 0.4 mol). The reaction was stirred at room temperature overnight. An additional 220 mg of picolyl chloride hydrochloride was added, and the reaction was stirred for 3 h. Water (25 mL) and ethyl acetate (50 mL) were added, and the layers were separated. The ethyl acetate fraction was washed with brine, dried over $MgSO_4$, and concentrated. The residue was purified by chromatography on silica, eluting with 35% ethyl acetate in hexane, to give 1.07g (92%) of N-[4-(4-bromophenoxy)benzenesulfonyl]-N-(pyridin-3-yl)methyl-D-valine t-butyl ester as a tan foam.

(iii) Preparation of 2(R)-N-(tert-butoxy)-2-[4-(4-bromophenoxy)benzenesulfonyl][(pyridin-3-yl)methyl] amino-3-methylbutanamide Dry hydrogen chloride was bubbled through a −20° C. solution of N-[4-(4-bromophenoxy)benzenesulfonyl]-N-(pyridin-3-yl)methyl-D-valine t-butyl ester (920 mg, 1.6 mol) in 20 mL of dichloromethane for 10 min, and the reaction was sealed and stirred at room temperature overnight. The reaction was vented, nitrogen was bubbled through the solution for 20 min, and the solution was concentrated to give N-[4-(4-bromophenoxy) benzenesulfonyl]-N-(pyridin-3-yl)methyl-D-valine hydrochloride that was used without further purification in the next step. The above acid was dissolved in 8 mL of dichloromethane, treated with O-t-butyl hydroxylamine hydrochloride (600 mg, 4.8 mol), N-methylmorpholine (0.92 mL, 8.3 mol), and EDC (613 mg, 3.2 mol), and stirred at room temperature overnight. The reaction was partitioned between water and dichloromethane, and the organic phase was washed with brine, dried over $MgSO_4$, and concentrated. The residue was purified by chromatography on silica, eluting with 5% methanol in dichloromethane, to give 750 mg (79%) of 2(R)-N-(tert-butoxy)-2-[4-(4-bromophenoxy)benzenesulfonyl][(pyridin-3-yl)methyl] amino-3-methylbutanamide as a clear oil.

The following compound was prepared in a similar manner:

Example 3(b) 2(R)-N-hydroxy-2-[(4-phenoxy) benzenesulfonyl][(pyridin-3-yl)methyl]amino-3-methylbutanamide

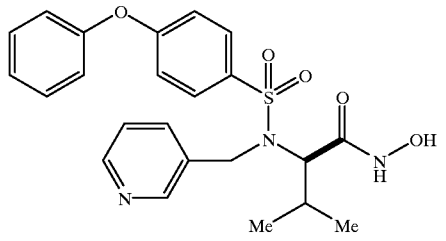

El MS m/e 473 ($M^+$)

Anal. Calcd. for $C_{23}H_{25}N_3O$, S•HCl•0.5 $H_2O$: C, 55.14; H, 5.03; N, 78.39. Found: C, 55.40; H, 5.42; N, 8.49.

Example 4

2(R)-2-[(diethylphosphonomethyl)(4-phenoxybenzenesulfonyl)amino]-N-hydroxyacetamide

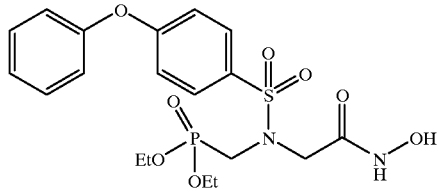

A solution of benzyl 2-[(diethylphosphonomethyl)(4-phenoxy-benzenesulfonyl)amino]acetate (1.0 g, 1.8 mmol) in 20 ml of ethyl acetate and 250 mg of 10% Pd on carbon was stirred under 1 atm of hydrogen for 3 h. The reaction was filtered through celite and concentrated. The residue, 2(R)-2-[(diethylphosphonomethyl)(4-phenoxybenzenesulfonyl)amino]-acetic acid, was dissolved in 20 mL of dichloromethane and treated with O-benzylhydroxylamine (0.25 g, 2.0 mmol), EDC (0.80 g, 4.1 mol), and 4-dimethylaminopyridine (50 mg, 0.4 mol). After 3 h, the reaction was partitioned between 50 mL of water and 100 mL ethyl acetate. The organic layer was dried over magnesium sulfate and concentrated. The residue was dissolved in 20 mL of 5% ethanol in ethyl acetate, and 250 mg of 10% Pd on carbon was added, and the reaction was stirred under 1 atm of hydrogen. The reaction was stopped at approximately 70% conversion when TLC analysis indicated that over-reduction of the product to the primary amide was beginning to occur. The mixture was filtered through celite and concentrated, and the residue was purified by PTLC (10% methanol in dichloromethane) to provide 360 mg (42%) of 2 (R)-2-[(diethylphosphonomethyl)(4-phenoxybenzenesulfonyl)amino]-N-hydroxyacetamide as a white foam: FAB MS m/e 473 $(M+H)^+$ The starting material was prepared as follows:

(i) Preparation of Diethyl[(4-phenoxy)benzenesulfonyl] aminomethylphosphonate

A solution of diethyl (N-benzyl) aminomethylphosphonate (2.5 g, 9.7 mmol) in 30 ml of EtOH and 0.5 g of $Pd(OH)_2$ was stirred under an atmosphere of hydrogen (1 atm) overnight. The reaction was filtered through celite and concentrated to give diethyl aminomethylphosphonate (600 mg, 3.6 mol). The crude phosphonate was dissolved in 30 ml of dichloromethane, cooled to 0° C., and treated with 4-phenoxybenzenesulfonyl chloride (800 mg, 3 mol) and triethylamine (1 ml, 7.2 mol). The ice bath was removed, the reaction was stirred for 4 h, and 20 mL of 5% HCl was added. The aqueous layer was extracted with 30 mL of dichloromethane, and the combined dichloromethane fractions were washed with brine, dried over magnesium sulfate, and concentrated to give diethyl[(4-phenoxy) benzenesulfonyl]aminomethylphosphonate (1.26 g, 88%) as a clear oil.

(ii) Preparation of Benzyl 2(R)-2-[(diethylphosphonomethyl)(4-phenoxybenzenesulfonyl) amino]acetate A 0° C. solution of diethyl[(4-phenoxy)benzenesulfonyl] aminomethylphosphonate (1.26 g, 3.2 mol) in 20 mL of DMF was treated with NaH (130 mg, 3.3 mol) and stirred for 30 min. Benzyl 2-bromoacetate (6.76 g, 3.3 mol) was added, and the reaction was stirred for 2 h at 0° C. and allowed to warm to room temperature. After 16 h, the reaction was partitioned between 100 mL of ethyl acetate and 50 mL of 5% aq. HCl. The organic layer was washed with brine, dried over magnesium sulfate, and concentrated. The residue was chromatographed on silica, eluting with 40% to 70% ethyl acetate in hexane, to give benzyl 2(R)-2-[(diethylphosphonomethyl)(4-phenoxybenzenesulfonyl) amino]acetate (1.0 g, 56%) as a clear oil.

Example 4(a) 2(R)-2-[(diethylphosphonomethyl)(4-phenoxybenzenesulfonyl)-amino]-acetic acid

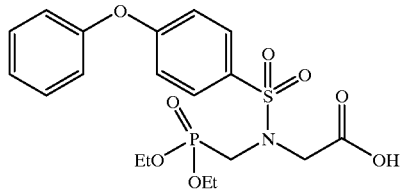

This compound can be prepared as described in Example 4 above.

Example 5

2(R)-1-[4-(4-Bromophenoxy)benzenesulfonyl]-N-hydroxypiperidine-2-carboxamide

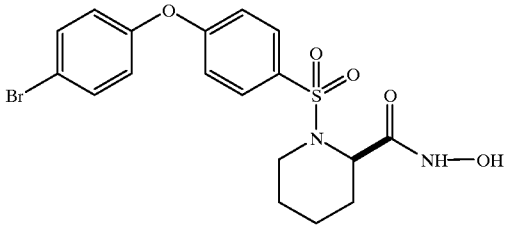

To a solution of 2(R)-1-[4-(4-bromophenoxy) benzenesulfonyl]piperidine-2-carboxylic acid (100 mg) in dimethylformamide (1 ml, dry), was added N-methylmorpholine (0.05 ml), followed by the BOP reagent (0.156 g), and this mixture was stirred for 15 minutes at room temperature. Hydroxylamine hydrochloride was added to the reaction as a solid followed by additional N-methylmorpholine (0.076 ml). The reaction was stirred for three hours, and TLC showed no trace of starting material. The reaction mixture was poured into sodium bicarbonate solution (1M, 10 ml), extracted with ethyl acetate/hexanes (5:1), (3×50 ml), and the combined organic fractions were washed with brine, then water, and dried over sodium sulfate. The solvent was removed, the residue was chromatographed with 4% ethanol in dichloromethane, the solvent was removed from the combined product fractions, and the residue was solvated in refluxing ethyl acetate. Isooctane was added to this mixture until milky, and the solvent was removed under vacuum to give 2(R)1-[4-(4-bromophenoxy)benzenesulfonyl]-piperidine-2-carboxylic acid hydroxyamide (0.065 g) as an off-white foam: mp 88–92° C.; $^1$H NMR (MeOD-$d_4$): δ 7.76 (dd, J=2 Hz, 9 Hz, 2H), 7.52 (dd, J=2 Hz, 9 Hz, 2H), 7.05 (dd, J=2 Hz, 9 Hz, 2H), 7.01 (dd, J=2 Hz, 9 Hz, 2H), 4.39(br s, 1H), 3.73 (d, J=10 Hz, 1H), 3.45–3.33 (m, 1H), 1.94–1.84 (m, 1H), 1.6–1.45 (m, 4H), 1.35–1.22 (m, 1H).

Anal. calc. for $C_{18}H_{19}BrN_2O_5S$: C, 47.48; H, 4.21; N, 6.15; S, 7.04. Found C, 47.66; H, 4.36; N, 6.15; S, 6.96.

The starting material was prepared as follows:

(i) Preparation of 2(R)-1-[4-(4-Bromophenoxy) benzenesulfonyl]piperidine-2-carboxylic acid To a stirred suspension of the 2(R)-pipecolic acid (4.0 g) in dichloromethane (200 ml) at 0° C. was added trimethylsilyl chloride (4.3 ml). After complete addition of the trimethylsilyl chloride, the reaction became homogeneous, and the reaction was warmed to room temperature. Triethylamine (10.58 ml) was added, and the reaction was stirred for 15 minutes followed by the addition of the 4-(4-bromophenoxy)-benzenesulfonyl chloride (10.76 g) as a solution in dichloromethane (100 ml). After two hours, the reaction mixture was poured into pH 4 citrate buffer (0.5 M), and this was extracted with dichloromethane (3×250 ml). The combined organic layers were dried over sodium sulfate and concentrated. The residue was chromatographed on silica, eluting with 8% ethanol in dichloromethane. Recrystallization from ethyl acetate/isooctane provided, in three crops, 13.51 g of 2(R)1-[4-(4-bromophenoxy) benzenesulfonyl]piperidine-2-carboxylic acid (13.51 g) as an off-white solid: mp 185° C.; $^1$H NMR ($CDCl_3$) δ 7.75 (dd, J=2 Hz, 9 Hz, 2H), 7.5 (dd, J=2 Hz, 9 Hz, 2H), 7.0 (dd, J=2 Hz, 9 Hz, 2H), 6.96 (dd, J=2 Hz, 9 Hz, 2H), 4.78 (d, J=5 Hz, 1H), 3.72 (d, J=3 Hz, 1H), 3.19 (ddd, J=3 Hz, 12.5 Hz, 13 Hz, 1H), 2.18 (dd, J=2 Hz, 13 Hz, 1H), 1.83–1.60 (m, 3H), 1.55–1.22 (m, 2H).

Anal. calc. for $C_{18}H_{18}BrNO_5S$: C, 49.10; H, 4.12; N, 3.18; Found: C, 48.97; H, 4.12; N, 3.19.

Example 5(a) 2(R)-1-[4-(4-Bromophenoxy) benzenesulfonyl]-N-hydroxypiperidine-2-carboxylic acid

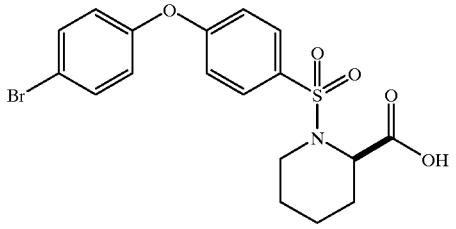

This compound can be prepared as described in Example 5 above.

Example 6

2(R)-1-[4-(Biphenyl-4-yl)oxybenzenesulfonyl]-N-hydroxy-piperidine-2-carboxamide

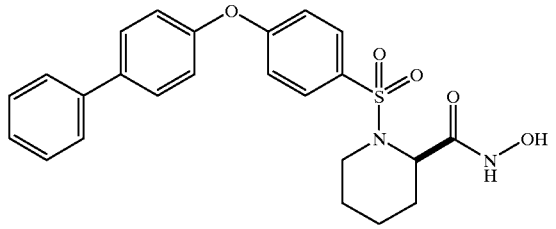

To a solution of 2(R)-N-(t-butyldiphenylsilyl)oxy-1-[4-(biphenyl-4-yl)oxybenzenesulfonyl]piperidine-2-carboxamide (0.21 g) in ethyl acetate/methanol (1:1, 50 ml), was added Amberlite ($F^-$) resin in three portions (3×0.025 g), over one hour. After four hours, the reaction was complete by TLC, the resin was removed by filtration, and the filtrate was concentrated. The residual oil was chromatographed with 7% ethanol, and 5% ethyl acetate in dichloromethane to give, after concentration from dichloromethane/t-butyl methyl ether, 2(R)-1-[4-(biphenyl-4-yl)oxybenzenesulfonyl]-N-hydroxy-piperidine-2-carboxamide (0.115 g) as an off-white foam:

$^1$H NMR ($CDCl_3$): δ 9.25 (s, 1H), 7.8 (d, J=9 Hz, 2H), 7.64 (d, J=8 Hz, 2H), 7.58 (d, J=7 Hz, 2H), 7.5–7.35 (m, 4H), 7.15 (d, J=11 Hz, 2H), 7.11 (d, J=11 Hz, 2H), 4.58 (d, J=4 Hz, 1H), 3.9–3.82 (d, J=14 Hz,1H), 3.11 (dd, J=13, 13 Hz, 1H), 2.27 (d, J=13 Hz, 1H), 1.85–1.2 (m, 5H).

Anal. calc. for $C_{24}H_{24}N_2O_5S$•0.65 MTBE: C, 64.20; H,6.29; N, 5.50; S, 6.29. Found: C, 64.51; H, 6.28; N, 5.76; S, 6.57.

The starting material was prepared as follows:

(i) Preparation of 2(R)1-[4-(Biphenyl4-yloxy)-benzenesulfonyl]-piperidine-2-carboxylic acid To a suspension of 2(R)1-[4-(4-Bromo-phenoxy)-benzenesulfonyl]-piperidine-2-carboxylic acid (0.44 g) in benzene (4 ml), a solution of sodium carbonate (2M, 2 ml) was added. Argon gas was bubbled through the stirred reaction mixture, and tetrakistriphenylphosphine palladium (0) (0.116 g) was added, followed by phenylboronic acid (0.36 g) as a solution in ethanol (4 ml). The reaction mixture was heated to reflux for 24 hours, cooled and poured into pH=4 buffer (1M, 50 ml), and extracted with dichloromethane (3×100 ml), and the combined organic extracts were washed with water, dried over sodium sulfate, and the solvent removed. The residue was chromatographed with 5% methanol in dichloromethane with 0.1% acetic acid. The product fractions were stripped down, ethyl acetate was added, followed by isooctane, and the solution was stripped down to give 2(R)1-[4-(Biphenyl-4-yloxy)-benzenesulfonyl]-piperidine-2-carboxylic acid as a beige foam: mp 77–81° C.; $^1$H NMR ($CDCl_3$): δ 7.76 (dd, J=2 Hz, 9 Hz, 2H), 7.65–7.57 (m, 4H), 7.5–7.4 (m, 2H), 7.38–7.3 (m, 1H), 7.12 (dd, J=2 Hz, 9.5 Hz, 2H), 7.06 (dd, J=2 Hz, 9 Hz, 2H), 4.8 (d, J=5 Hz, 1H), 3.74 (d, J=12 Hz, 1H), 3.21( dd, J=11 Hz, J =12 Hz, 1H), 2.2 (d, J=12 Hz, 1H), 1.8–1.6 (m, 3H), 1.55–1.25 (m, 2H).

Anal. calc. for $C_{24}H_{23}NO_5S$: C, 65.88; H, 5.30; N, 3.20. Found: C, 65.97; H, 5.53; N, 3.14.

(ii) 2(R)-1-[4-(Biphenyl-4-yloxy)-benzenesulfonyl]-N-(t-buyldiphenylsilyl)oxy-piperidine-2-carboxamide To a solution of 2(R)1-[4-(Biphenyl4-yloxy)-benzenesulfonyl]-piperidine-2-carboxylic acid (0.219 g) in dichloromethane (10 ml), dimethylformamide (0.008 ml) was added, and the solution was cooled to −5° C. Oxalyl chloride (0.066 ml) was added, and the reaction was stirred for 30 minutes, then cooled to −78° C., and a solution of the diphenyl-t-butyl silyl chloride (0.217 g) and pyridine (0.121 ml) in dichloromethane (4 ml) was added. The reaction was monitored by TLC and after two hours was complete. The reaction was poured into ethyl acetate/hexanes (3:1, 100 ml); washed with ammonium chloride (2M, 20 ml), sodium bicarbonate (2M, 20 ml), and brine (20 ml); and dried over sodium sulfate. The solvent was removed, and the residue was chromatographed using ethyl acetate/dichloromethane/hexanes (1:5:4), the product containing fractions were collected and the solvent removed. The product oil was diluted with dichloromethane, isooctane was added, and the mixture was stripped down to give the product 2(R)-N-(t-butyldiphenylsilyl)oxy-1-[4-(Biphenyl-4-yloxy)-benzenesulfonyl]-piperidine-2-carboxamide (0.261 g) as a beige foam: mp 80–84° C.; $^1$H NMR ($CDCl_3$): δ 7.8–7.72 (m, 4H), 7.7–7.55 (m, 5H), 7.48–7.32 (m, 10H), 7.12 (d, J=8.5 Hz, 2H), 7.02 (d, J=8.5 Hz, 2H), 4.26 (m, 1H), 3.54 (m, 1H), 3.34 (m, 1H), 2.1 (m, 1H), 1.6 (m, 1H), 1.4 (m, 1H), 1.17(s, 9H), 1.15–1.0 (m, 4H).

Example 6(a) 2(R)-1[4-(Biphenyl-4-yl) oxybenzenesulfonyll-N-hydroxy-piperidine-2-carboxylic acid

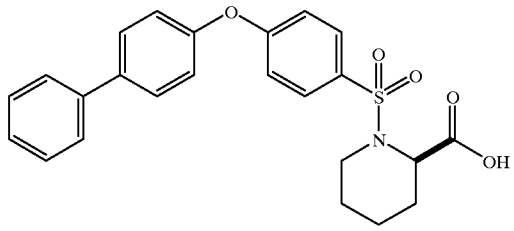

This compound can be prepared as described in Example 6 above.

Example 7

2(R)-1-(4-Phenoxy-benzenesulfonyl)-N-hydroxy-piperidine-2-carboxamide

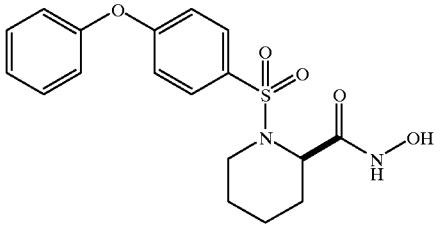

To a solution of 2(R)-N-(t-butyldiphenylsilyl)oxy-1-(4-Phenoxy-benzenesulfonyl)-piperidine-2-carboxamide (0.305 g) in ethyl acetate/methanol (15:85, 50 ml), was added fluorine (F−) resin in three portions (3×0.05 g), over one hour. After 3.5 hours, the reaction was complete by TLC, and the resin was filtered-off, rinsed with methanol, and the solvent removed. The residual oil was chromatographed with 7% methanol and 5% ethyl acetate in dichloromethane. The product fractions were combined, and dichloromethane was added, followed by isooctane, and the mixture was stripped-down to give the product 2(R)-1-(4-Phenoxy-benzenesulfonyl)-N-hydroxy-piperidine-2-carboxamide (0.091 g), as a beige foam: $^1$H NMR ($CDCl_3$): δ 9.32 (s, 1H), 7.78 (d, J=9Hz, 2H), 7.42 (dd, J=8, 8Hz, 2H), 7.22–7.19 (m, 1H), 7.08 (d, J=8.5 Hz, 2H), 7.05 (d, J=9 Hz, 2H), 4.58 (d, J=4 Hz, 1H), 3.85 (d, J=14 Hz, 1H), 3.18–3.04 (m, 1H), 2.26 (d, J=13 Hz, 1H), 1.7–1.0 (m, 5H).

Anal. calc. for $C_{18}H_{20}N_2O_5S$•0.26 methanol+0.13 isooctane: C, 58.01; H, 5.90; N, 7.01; S, 8.02. Found: C, 58.07; H, 5.78; N, 7.05; S, 7.99.

The starting material was prepared as follows:

(i) Preparation of 2(R)-1-(4-Phenoxy-benzenesulfonyl)-piperidine-2-carboxylic acid To a solution of 2(R)1-[4-(4-Bromophenoxy)-benzenesulfonyl]-piperidine-2-carboxylic acid (0.22 g) in ethyl acetate (50 ml), was added 10% palladium on carbon catalyst (20% by weight, 0.044 g). The mixture was evacuated, charged with hydrogen gas, and stirred for 24 hours under balloon pressure of hydrogen. The catalyst was filtered-off and the solvent removed. The residue was chromatographed using 5% ethanol in dichloromethane with 0.1% acetic acid. The solvent was removed from the combined product fractions, isooctane was added, and the solution was stripped-down to yield 2(R)-1-(4-phenoxybenzenesulfonyl)-piperidine-2-carboxylic acid (0.145 g) as a yellow foam: $^1$H NMR ($CDCl_3$):δ 7.74 (d, J=9 Hz, 2H), 7.41 (dd, J=8, 8 Hz, 2H), 7.21 (dd, J=7.5, 7.5 Hz, 1H), 7.06 (d, J=8 Hz, 2H), 7.0 (d, J=9 Hz, 2H), 4.78 (d, J=4 Hz, 1H), 3.73 (d, J=12.5 Hz, 1H), 3.19 (ddd, J=2.5, 10.5, 12.5 Hz, 1H), 2.18 (d, J=14 Hz, 1H), 1.8–1.2 (m, 5H).

(ii) Preparation of 2(R)-N-(t-Butyldiphenylsilyl)oxy-1-(4-phenoxy-benzenesulfonyl)-piperidine-2-carboxamide To a solution of the yield 2(R)-1-(4-phenoxy-benzenesulfonyl)-piperidine-2-carboxylic acid (0.21 g) in dichloromethane (10 ml), dimethylformamide (0.008 ml) was added and the solution cooled to −5° C. Oxalyl chloride (0.075 ml) was added, and the reaction was stirred for 30 minutes, then cooled to −78° C., and a solution of diphenyl-t-butyl silyl chloride (0.251 g) and pyridine (0.141 ml) in dichloromethane (4 ml) was added. The reaction was monitored by TLC and after two hours was complete. The reaction was poured into ethyl acetate/hexanes (3:1, 100 ml); washed with ammonium chloride (2M, 20 ml), sodium bicarbonate (2M, 20 ml), and brine (20 ml); and dried over sodium sulfate. The solvent was removed from the product oil, which was diluted with dichloromethane, isooctane was added, and the mixture was stripped down to give the product 2(R)-N-(t-butyldiphenylsilyl)oxy-1-(4-phenoxy-benzenesulfonyl)-piperidine-2-carboxamide (0.31 g) as an oil, which was used without further purification.

The results obtained during biological testing of some preferred embodiments of the inventive compounds are described below.

BIOLOGICAL DATA

Isolation of MMP's for Assays

The catalytic domain of human collagenase-1 was expressed as a fusion protein with ubiquitin in *E. coli* (see Gehring, E. R., *J. Biol. Chem.,* 1995, 270, 22507, which article is entirely incorporated herein by reference). After purification of the fusion protein, the fibroblast collagenase-1 catalytic domain (HFC) was released either by treatment with purified, active stromelysin-1 (1:50 w/w ratio), which generated nearly 100% N-terminal Phe1, or by autoprocessing the concentrated collagenase-1 fusion and then incubating at 37° C. for 1 hour. Final purification was completed using zinc chelate chromatography.

The propeptide and catalytic domain of human collagenase-3 (Coll3) was expressed in *E. coli* as an N-terminal fusion protein with ubiquitin. After purification of the fusion from inclusion bodies, the catalytic domain was liberated by treatment with 2mM APMA at room temperature overnight. Final purification was completed using copper chelate chromatography.

The catalytic domain of human stromelysin (Sln) was obtained by expression and purification of a C-terminally truncated prostromelysin-1 from *E. coli* host BL21 (see Marcy et al. *Biochem.,* 1991, 30, 6476, which article is entirely incorporated herein by reference). The subsequent activation of the mature form (Sln) was completed with 2mM APMA for 1 hour at 37° C., followed by separation using a sizing column.

Human matrilysin (Matr) was expressed in *E. coli* as a fusion protein with ubiquitin. After purification of the matrilysin/ubiquitin fusion from inclusion bodies, the catalytic domain was liberated by treatment with 2mM APMA at 37 ° C. for 2 hours. Final purification was complete using copper chelate chromatography.

The catalytic and fibronectin-like portion of human progelatinase A (GelA) was expressed as a fusion protein with ubiquitin in *E. Coli.* Assays were carried out on autocatalytically activated material.

Compounds of Formula I exhibited the ability to inhibit MMPs when tested in the following assay.

In Vitro Assay Procedure

Assays were performed in assay buffer (50 mM Tricine pH 7.5, 200 mM sodium chloride, 10 mM calcium chloride, 0.5 mM zinc acetate containing 2% dimethyl sulfoxide (DMSO)), once the substrate and inhibitor were diluted into it. Stock solutions of inhibitors were prepared in 100 % DMSO. Stock solutions of the substrate were prepared in 100 % DMSO at a concentration of 6 mM.

The assay method was based on the hydrolysis of MCA-Pro-Leu-Gly-Leu-DPA-Ala-Arg-$NH_2$ (American Peptide Co.) at 37° C. (see Knight, C. G. et al., *FEBS,* 1992, 296, 263–266, which article is entirely incorporated herein by reference). The fluorescence changes were monitored with a Perkin-Elmer LS-50B fluorimeter using an excitation wavelength of 328 nm and an emission wavelength of 393 nm. The substrate concentration used in the assays was 10 $\mu$M. The inhibitor was diluted into the assays from a solution in 100 % DMSO, and controls substituted an equal volume of DMSO so that the final DMSO concentration from inhibitor and substrate dilution in all assays was 2%. The concentration of enzyme in the assay ranged from 60 pM for gelatinase A to 1.5 nM for stromelysin and is a function of the enzymes respective $k_{cat}/K_m$ for the MCA peptide substrate. Proper determination of steady-state rates of substrate cleavage required assay lengths of 60 minutes to allow for complete equilibration of the enzyme-inhibitor complex.

The $K_m$ for the MCA peptide substrate with the matrix metalloproteinases is quite high and exceeds its solubility under assay conditions. Consequently, the apparent $K_i$ ($K_{i,app}$) was determined to describe the strength of inhibition. However, in this case, $K_{i,app}$ would be essentially equal to $K_i$ since $[S] \ll K_m$. For the determination of $K_{i,app}$, the concentration of the inhibitor was varied at a constant and low concentration of substrate, and the steady-state rates of fluorescence change were determined. In most cases, absorptive quench due to the presence of ligand was not observed. For slow-binding inhibitors, onset of inhibition curves were collected for at least 45 minutes so that equilibrium was established. Steady-state rates of fluorescence change were obtained by fitting a curve to an equation for a single exponential decay containing a linear phase. The fitted value of the linear phase was taken as the steady-state rate. The steady-state rates were fitted to the Michaelis equation describing competitive inhibition by non-linear methods. Data resulting from tight-binding inhibition was analyzed, and $K_{i,app}$ determined by fitting the data to the tight-binding equation of Morrison (*Biochem. Biophys. Acta,* vol. 185, pp. 269–286 (1969), which article is entirely incorporated herein by reference) by non-linear methods.

The results of the above-described tests are presented below in Table 1. All Ki values are in nM units.

TABLE 1

| | Ki values (nM) | | | | |
|---|---|---|---|---|---|
| Example # | Strom | HFC | Matr | Gel A | Coll-3 |
| 3(a) | 0.35 | 7.6 | | | 0.02 |
| 3(b) | 1.2 | 6.0 | | | 0.05 |
| 4 | 0.23 | 27 | | | 0.09 |
| 4(a) | 27,000 | | | | 740 |
| 5 | 0.04 | 15 | 44 | 0.018 | 0.014 |
| 5(a) | 16,000 | 481,000 | 540,000 | 192 | 448 |
| 6 | 0.06 | 8.8 | 6.7 | 0.014 | 0.008 |
| 6(a) | 2190 | 125,000 | 72,000 | 64 | 212 |
| 7 | 0.07 | 6.6 | 55 | 0.007 | 0.007 |

In describing the invention, applicant has set forth certain theories in an effort to disclose how or why the invention works in the manner in which it works. These theories are set forth for informational purposes only. Applicant is not to be bound by any specific chemical or physical mechanisms or theories of operation.

While the invention has been described in terms of various preferred embodiments and specific examples, those skilled in the art will recognize that various changes and modifications can be made without departing from the spirit and scope of the invention, as defined in the appended claims.

What is claimed is:

1. A compound of formula 1:

(I)

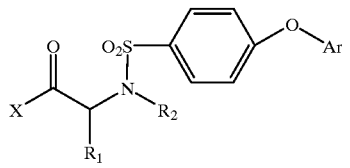

wherein:

Ar is an aryl group or a heteroaryl group;

X is —NH—OH or —OH:

$R_1$ is H, —$CH(R_3)(R_4)$, —$C(O)R_3$, a cycloalkyl group, a heterocycloalkyl group, an aryl group, or a heteroaryl group, wherein $R_3$ is H or any suitable substituent and $R_4$ is H, an alkyl group, a cycloalkyl group, a heterocycloalkyl group, an aryl group, or a heteroaryl group;

$R_2$ is $CH_2$-$R_5$, wherein $R_5$ is H or any suitable substituent, or wherein R. and $R_4$ are optionally substituted carbon atoms singly- or double-bonded to one another;

or a pharmaceutically acceptable prodrug, salt or solvate thereof.

2. A compound according to claim 1, wherein $R_3$ is hydrogen, an alkyl group, a cycloalkyl group, a heterocycloalkyl group, an aryl group, a heteroaryl group, —$OR_{10}$, —$SR_{10}$, C≡C-$R_{10}$, —$C(O)OR_{10}$, $C(O)NHR_{10}$, wherein $R_{10}$ is hydrogen, an alkyl group, a cycloalkyl group, a heterocycloalkyl group, an aryl group, or a heteroaryl group; or a pharmaceutically acceptable prodrug, salt, or solvate thereof.

3. A compound according to claim 1, wherein said compound has the formula II:

(II)

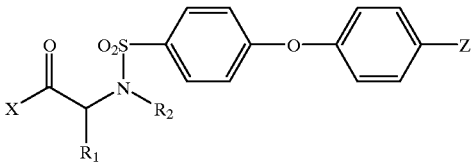

wherein $R_1$, $R_2$, and X are as defined in claim 1 and Z is a halogen group, an alkyl group, a cycloalkyl group, a heterocycloalkyl group, an O-alkyl group, an S-alkyl group, an aryl group, or a heteroaryl group; or a pharmaceutically acceptable prodrug, salt, or solvate thereof.

4. A compound according to claim 1, wherein Ar is a heteroaryl group containing six ring atoms; or a pharmaceutically acceptable prodrug, salt, or solvate thereof.

5. A compound according to claim 4, wherein Ar is pyridyl, pyrimidinyl, pyridazinyl, or pyrazinyl; or a pharmaceutically acceptable prodrug, salt, or solvate thereof.

6. A compound according to claim 1, wherein $R_5$ is H and $R_4$ is an alkyl group; or a pharmaceutically acceptable prodrug, salt, or solvate thereof.

7. A compound according to claim 1, wherein $R_5$ is a heteroaryl group; or a pharmaceutically acceptable prodrug, salt, or solvate thereof.

8. A compound according to claim 1, wherein $R_5$ is —$CHR_6R_7$, wherein $R_6$ is H or any suitable substituent and $R_7$ is

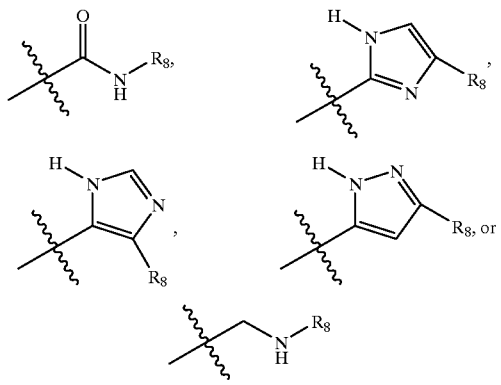

wherein $R_8$ is any suitable substituent; or a pharmaceutically acceptable prodrug, salt, or solvate thereof.

9. A compound according to claim 1, wherein $R_4$ is an alkyl group and $R_3$ is an alkyl group, an O-alkyl group, or an S-alkyl group; or a pharmaceutically acceptable prodrug, salt, or solvate thereof.

10. A compound according to claim 9, wherein $R_3$ is a —$CH_2CH_2$-heteroaryl group, an —$OCH_2$—; heteroaryl group, or an —S—$CH_2$-heteroaryl group; or a pharmaceutically acceptable prodrug, salt, or solvate thereof.

11. A compound according to claim 1, wherein $R_4$ and $R_5$ together form the group —$CH_2CH_2$—; or a pharmaceutically acceptable prodrug, salt, or solvate thereof.

12. A compound according to claim 1, wherein the compound is:

2(R)-1-[4-(4-Bromophenoxy)benzenesulfonyl]-N-hydroxy-piperidine-2-carboxamide,

2(R)-1-[4-(4-Chlorophenoxy)benzenesulfonyl]-N-hydroxy-piperidine-2-carboxamide,

2(R)-1-[4-(4-Fluorophenoxy)benzenesulfonyl]-N-hydroxy-piperidine-2-carboxamide,

2(R)-1-[4-(4-Methylphenoxy)benzenesulfonyl]-N-hydroxy-piperidine-2-carboxamide,

2(R)-1-[4-(4-Methoxyphenoxy)benzenesulfonyl]-N-hydroxy-piperidine-2-carboxamide, 2(R)-1-[4-Phenoxybenzenesulfonyl]-N-hydroxy-piperidine-2-carboxamide, 2(R)-1-[4-(Biphenyl-4-yl)oxybenzenesulfonyl]-N-hydroxy-piperidine-2-carboxamide, 2(R)-1-[4-(4-(Imidazol-1-yl)phenoxy)benzenesulfonyl]-N-hydroxy-piperidine-2-carboxamide, 2(R)-1-[4-(4-(Imidazol-2-yl)phenoxy)benzenesulfonyl]-N-hydroxy-piperidine-2-carboxamide, 2(R)-1-[4-(4-(Imidazol-4-yl)phenoxy)benzenesulfonyl]-N-hydroxy-piperidine-2-carboxamide, 2(R)-1-[4-(4-(Pyrazol-4-yl)phenoxy)benzenesulfonyl]-N-hydroxy-piperidine-2-carboxamide, 2(R)-1-[4-(4-(Pyrazol-3-yl)phenoxy)benzenesulfonyl]-N-hydroxy-piperidine-2-carboxamide, 2(R)-1-[4-(4-(2-(Dimethylamino)ethyl)phenoxy)benzenesulfonyl]-N-hydroxy-piperidine-2-carboxamide, 2(R)-1-[4-(Pyrid-4-yl)oxybenzenesulfonyl]-N-hydroxypiperidine-2-carboxamide, 2(R), 3(S)-1-[4-(4-Chlorophenoxy)benzenesulfonyl]-N-hydroxy-3-methyl-piperidine-2-carboxamide, 2(R), 3(S)-1-[4-(4-Fluorophenoxy)benzenesulfonyl]-N-hydroxy-3-methyl-piperidine-2-carboxamide, 2(R), 3(S)-1-[4-(4-Methoxyphenoxy)benzenesulfonyl]-N-hydroxy-3-methyl-piperidine-2-carboxamide, 2(R), 3(S)-1-[4-(4-(Imidazol-1-yl)phenoxy)benzenesulfonyl]-N-hydroxy-3-methyl-piperidine-2-carboxamide, 2(R), 3(S)-1-[4-(4-(Imidazol-2-yl)phenoxy)benzenesulfonyl]-N-hydroxy-3-methyl-piperidine-2-carboxamide, 2(R), 3(S)-1-[4-(4-(Imidazol-4-yl)phenoxy)benzenesulfonyl]-N-hydroxy-3-methyl-piperidine-2-carboxamide, 2(R), 3(S)-1-[4-(4-(Pyrazol-4-yl)phenoxy)benzenesulfonyl]-N-hydroxy-3-methyl-piperidine-2-carboxamide, 2(R), 3(S)-1-[4-(4-(Pyrazol-3-yl)phenoxy)benzenesulfonyl]-N-hydroxy-3-methyl-piperidine-2-carboxamide, 2(R), 3(S)-1-[4-(Pyrid-4-yl)oxybenzenesulfonyl]-N-hydroxy-3-methyl-piperidine-2-carboxamide, 2(R)-2-[4-(4-Bromophenoxy)benzenesulfonyl][(pyridin-3-yl)methyl]amino-N-hydroxy-3-methylbutanamide, 2(R)-2-[4-(4-Chlorophenoxy)benzenesulfonyl][(pyridin-3-yl)methyl]amino-N-hydroxy-3-methylbutanamide, 2(R)-2-[4-(4-Chlorophenoxy)benzenesulfonyl][(pyridin4-yl)methyl]amino-N-hydroxy-3-methylbutanamide, 2(R)-2-[4-(4-Chlorophenoxy)benzenesulfonyl][(imidazol-2-yl)methyl]amino-N-hydroxy-3-methylbutanamide, 2(R)-2-[4-(4-Chlorophenoxy)benzenesulfonyl][2-(imidazol-2-yl)ethyl]amino-N-hydroxy-3-methylbutanamide, 2(R)-2-[4-(4-Chlorophenoxy)benzenesulfonyl][2-(imidazol-4-yl)ethyl]amino-N-hydroxy-3-methylbutanamide, 2(R)-2-[4-(4-Chlorophenoxy)benzenesulfonyl][2-(pyrazol-3-yl)ethyl]amino-N-hydroxy-3-methylbutanamide, 2(R)-2-[4-(4-Chlorophenoxy)benzenesulfonyl][2-(methylcarbamoyl)ethyl]amino-N-hydroxy-3-methylbutanamide, 2(R)-2-[4-(4-Chlorophenoxy)benzenesulfonyl][2-(methylamino)ethyl]amino-N-hydroxy-3-methylbutanamide, 2(R)-2-[4-(4-Chlorophenoxy)benzenesulfonyl][(pyridin-3-yl)methyl]amino-N-hydroxy-2-cyclohexylacetamide, 2(R)-2-[4-(4-Chlorophenoxy)benzenesulfonyl][2-(imidazol-2-yl)ethyl]amino-N-hydroxy-2-cyclohexylacetamide, 2(R)-2-[4-(4-Chlorophenoxy)benzenesulfonyl][2-(methylcarbamoyl)ethyl]amino-N-hydroxy-2-cyclohexylacetamide, 2(R)-2-[4-(4-Chlorophenoxy)benzenesulfonyl][(pyridin-3-yl)methyl]amino-N-hydroxy-2-(tetrahydro-2H-pyran-4-yl)acetamide, 2(R)-2-[4-(4-Chlorophenoxy)benzenesulfonyl][2-(methylcarbamoyl)ethyl]amino-N-hydroxy-2-(tetrahydro-2H-pyran-4-yl)acetamide, 2(R)-2-[4-(4-Chlorophenoxy)benzenesulfonyl][(pyridin-3-yl)methyl]amino-N-hydroxy-2-(1-methylpiperidin-4-yl)acetamide, 2(R)-2-[4-(4-Chlorophenoxy)benzenesulfonyl][(pyridin-3-yl)methyl]amino-N-hydroxy-2-(1-acetylpiperidin-4-yl)acetamide, 2(R)-2-[4-(4-Chlorophenoxy)benzenesuifonyl][(2-(methylcarbamoyl)ethyl]amino-N-hydroxy-2-(1-methylpiperidin-4-yl)acetamide, 2(R), 3(R)-2-[4-(4-Chlorophenoxy)benzenesulfonyl](methyl)amino-N,3-dihydroxybutanamide, 2(R), 3(R)-2-[4-(4-Chlorophenoxy)benzenesulfonyl](methyl)amino-N-hydroxy-3-methoxybutanamide, 2(R), 3(R)-2-[4-(4-Chlorophenoxy)benzenesulfonyl](methyl)amino-N-hydroxy-3-(2-methoxyethoxy)butanamide, 2(R), 3(R), 3(2'(S))-2-[4-(4-Chlorophenoxy)benzenesulfonyl](methyl)amino-N-hydroxy-3-[(5-oxopyrrolidin-2-yl)methoxy]butanamide, 2(R), 3(R)-2-[4-(4-Chlorophenoxy)benzenesulfonyl](methyl)amino-N-hydroxy-3-[(1-methylimidazol-2-yl)methoxy]butanamide, 2(R)-2-[4-(4-Chlorophenoxy)benzenesulfonyl](methyl)amino-N-hydroxy-2-(1-methylpiperidin-4-yl)acetamide, 2(R)-2-[4-(4-Chlorophenoxy)benzenesulfonyl](methyl)amino-N-hydroxy-2-cyclohexylacetamide, 2(R)-2-[4-(4-Chlorophenoxy)benzenesulfonyl](methyl)amino-N-hydroxy-2-(tetrahydro-2H-pyran-4-yl)acetamide, 2(S) 3(R)-2-[4-(4-Chlorophenoxy)benzenesulfonyl)(methyl)amino-N-hydroxy-3-[(5-methylisoxazol-3-yl)methylsulfanyl]butanamide, 2(S), 3(R)-2-[4-(4-Chlorophenoxy)benzenesulfonyl](methyl)amino-N-hydroxy-3-[(pyrid-2-yl)methylsulfanyl]butanamide, 2(S), 3(R)-2-[4-(4-Chlorophenoxy)benzenesulfonyl](methyl)amino-N-hydroxy-3-[(1-methylimidazol-2-yl)methylsulfanyl]butanamide, 2(S), 3(R)-2-[4-(4-Chlorophenoxy)benzenesulfonyl](methyl)amino-N-hydroxy-3-[(1-methylpiperidin-4-yl)methylsulfanyl]butanamide, 2(S), 3(R)-2-[4-(4-Chlorophenoxy)benzenesulfonyl](methyl)amino-N-hydroxy-3-[2-(dimethylamino)ethylsulfanyl]butanamide, 2(S)-2-[4-(4-Chlorophenoxy)benzenesulfonyl](methyl)amino-N-hydroxy-3-[(5-methylisoxazol-3-yl)methylsulfanyl]propanamide, 2(S)-2-(4-(4-Chlorophenoxy)benzenesulfonyl](methyl)amino-N-hydroxy-3-[(pyrid-2-yl)methylsulfanyl]propanamide, 2(S)-2-[4-(4-Chlorophenoxy)benzenesulfonyl](methyl)amino-N-hydroxy-3-[(1-methylimidazol-2-yl)methylsulfanyl]propanamide, 2(R), 3(R)-2-[4-(4-Fluorophenoxy)benzenesulfonyl](methyl)amino-N,3-dihydroxybutanamide, 2(R), 3(R)-2-[4-(4-Fluorophenoxy)benzenesulfonyl](methyl)amino-N-hydroxy-3-methoxybutanamide, 2(R), 3(R)-2-[4-(4-Fluorophanoxy)bnenene sulfonyl](methyl)amino-N-hydroxy-3-(2-methoxyethoxy)butanamide, 2(R), 3(R), 3(2'(S))-2-[4-(4-Fluorophenoxy)benzenesulfonyl](methyl)amino-N-hydroxy-3-[(5-oxopyrrolidin-2-yl)methoxy]butanamide, 2(R), 3(R)-2-[4-(4-Fluorophenoxy)benzenesulfonyl](methyl)amino-N-hydroxy-3-[(1-methylimidazol-2-yl)methoxy]butanamide, 2(R)-2-[4-(4-Fluorophenoxy)benzenesulfonyl](methyl)amino-N-hydroxy-2-(1-methylpiperidin-4-yl)acetamide, 2(R)-2-[4-(4-Fluorophenoxy)benzenesulfonyl](methyl)amino-N-hydroxy-3-methylbutanamide, 2(R)-2-[4-(4-Fluorophenoxy)benzenesulfonyl](methyl)amino-N-hydroxy-2-cyclohexylacetamide, 2(R)-2-[4-(4-Fluorophenoxy)benzenesulfonyl](methyl)amino-N-hydroxy-2-(tetrahydro-2H-pyran-4-yl)acetamide, 2(S), 3(R)-2-[4-(4-Fluorophenoxy)benzenesulfonyl](methyl)amino-N-hydroxy-3-[(5-methylisoxazol-3-yl)methylsulfanyl]butanamide, 2(S), 3(R)-2-[4-(4-Fluorophenoxy)benzenesulfonyl](methyl)amino-N-hydroxy-3-[(pyrid-2-yl)methylsulfanyl]butanamide, 2(S), 3(R)-2-[4-(4-Fluorophenoxy)benzenesulfonyl](methyl)amino-N-hydroxy-3-[(1-methylimidazol-2-yl)methylsulfanyl]butanamide, 2(S), 3(R)-2-[4-(4-Fluorophenoxy)benzenesulfonyl](methyl)amino-N-hydroxy-3-[(1-methylpiperidin-4-yl)methylsulfanyl]butanamide, 2(S), 3(R)-2-[4-(4-Fluorophenoxy)benzenesulfonyl](methyl)amino-N-hydroxy-3-[2-(dimethylamino)ethylsulfanyl]butanamide, 2(S)-2-[4-(4-Fluorophenoxy)benzenesulfonyl](methyl)amino-N-hydroxy-3-[(5-methylisoxazol-3-yl)methylsulfanyl]propanamide, 2(S)-2-[4-(4-Fluorophenoxy)benzenesulfonyl](methyl)amino-N-hydroxy-3-[(pyrid-2-yl)methylsulfanyl]propanamide, 2(S)-2-[4-(4-Fluorophenoxy)benzenesulfonyl](methyl)amino-N-hydroxy-3-[(1-methylimidazol-2-yl)methylsulfanyl]propanamide, 2(R), 3(R)-2-[4-(Pyrid-4-yl)oxybenzenesulfonyl](methyl)amino-N,3-dihydroxybutanamide, 2(R), 3(R)-2-[4-(Pyrid-4-yl)oxybenzenesulfonyl](methyl)amino-N-hydroxy-3-methoxybutanamide, 2(R), 3(R)-2-[4-(Pyrid-4-yl)oxybenzenesulfonyl](methyl)amino-N-hydroxy-3-(2-methoxyethoxy)butanamide, 2(R), 3(R), 3(2'(S))-2-[4-(Pyrid-4-yl)oxybenzenesulfonyl](methyl)amino-N-hydroxy-3-[(5-oxopyrrolidin-2-yl)methoxy]butanamide, 2(R)-2-[4-(Pyrid-4-yl)oxybenzenesulfonyl](methyl)amino-N-hydroxy-3-methylbutanamide, 2(R)-2-[4-(Pyrid-4-yl)oxybenzenesulfonyl](methyl)amino-N-hydroxy-2-cyclohexylacetamide, 2(R)-2-[4-(Pyrid-4-yl)oxybenzenesulfonyl](methyl)amino-N-hydroxy-2-cyclopentylacetamide, 2(R)-2-[4-(Pyrid-4-yl)oxybenzenesulfonyl](methyl)amino-N-hydroxy-2-cyclopropylacetamide, 2(R)-2-[4-(Pyrid-4-yl)oxybenzenesulfonyl](methyl)amino-N-hydroxy-2-(tetrahydro-2H-pyran-4-yl)acetamide, 2(S), 3(R)-2-[4-(Pyrid-4-yl)oxybenzenesulfonyl](methyl)amino-N-hydroxy-3-[(5-methylisoxazol-3-yl)methylsulfanyl]butanamide, 2(S)-2-[4-(Pyrid-4-yl)oxybenzenesulfonyl](methyl)amino-N-hydroxy-3-[(5-(hydroxymethyl)isoxazol-3-yl)methylsulfanyl]propanamide, 2(S)-2-[4-(Pyrid-4-yl)oxybenzenesulfonyl](methyl)amino-N-hydroxy-3-[(phenyl)methylsulfanyl]propanamide, 2(S)-2-[4-(Pyrid-4-yl)oxybenzenesulfonyl](methyl)amino-N-hydroxy-3-[(4-fluorophenyl)methylsulfanyl]propanamide, 2(S)-2-[4-(Pyrid-4-yl)oxybenzenesulfonyl](methyl)amino-N-hydroxy-3-[(1-methylimidazol-2-yl)methylsulfanyl]propanamide, 2(R)-2-[4-(4-Bromophenoxy)benzenesulfonyl](methyl)amino-N-hydroxy-3-methylbutanamide, 2(R)-2-[4-(4-Chlorophenoxy)benzenesulfonyl](methyl)amino-N-hydroxy-3-methylbutanamide, 2(R)-2-[4-(4-Fluorophenoxy)benzenesulfonyl](methyl)amino-N-hydroxy-3-methylbutanamide, 2(R)-2-[4-(4-Methylphenoxy)benzenesulfonyl](methyl)amino-N-hydroxy-3-methylbutanamide, 2(R)-2-[4-(4-Methoxyphenoxy)benzenesulfonyl](methyl)amino-N-hydroxy-3-methylbutanamide, 2(R)-2-[4-Phenoxybenzenesulfonyl](methyl)amino-N-hydroxy-3-methylbutanamide, 2(R)-2-[4-(Biphenyl-4-yl)oxybenzenesulfonyl]-N-hydroxy-piperidine-2-carboxamide, 2(R)-2-[4-(4-(Imidazol-1-yl)phenoxy)benzenesulfonyl](methyl)amino-N-hydroxy-3-methylbutanamide, 2(R)-2-[4-(4-(Imidazol-2-yl)phenoxy)benzenesulfonyl](methyl)amino-N-hydroxy-3-methylbutanamide, 2(R)-2-[4-(4-(Imidazol-4-yl)phenoxy)benzenesulfonyl](methyl)amino-N-hydroxy-3-methylbutanamide, 2(R)-2-[4-(4-(2-(dimethylamino)ethyl)phenoxy)benzenesulfonyl](methyl)amino-N-hydroxy-3-methylbutanamide, 2(R)-1-[4-(4-Bromophenoxy)benzenesulfonyl]-N-hydroxy-hexahydro-1H-azepine-2-carboxamide, 2(R)-1-[4-(4-Chlorophenoxy)benzenesulfonyl]-N-hydroxy-hexahydro-1H-azepine-2-carboxamide, 2(R)-1-[4-(4-Fluorophenoxy)benzenesulfonyl]-N-hydroxy-hexahydro-1H-azepine-2-carboxamide, 2(R)-1-[4-(4-Methylphenoxy)benzenesulfonyl]-N-hydroxy-hexahydro-1H-azepine-2-carboxamide, 2(R)-1-[4-(4-Methoxyphenoxy)benzenesulfonyl]-N-hydroxy-hexahydro-1H-azepine-2-carboxamide, 2(R)-1-[4-Phenoxybenzenesulfonyl]-N-hydroxy-hexahydro-1H-azepine-2-carboxamide, 2(R)-1-(4-(Biphenyl-4-yl)oxybenzenesulfonyl]-N-hydroxy-hexahydro-1H-azepine-2-carboxamide, 2(R)-1-[4-(4-(Imidazol-1-yl)phenoxy)benzenesulfonyl]-N-hydroxy-piperidine-2-carboxamide, 2(R)-1-[4-(4-(Imidazol-2-yl)phenoxy)benzenesulfonyl]-N-hydroxy-hexahydro-1H-azepine-2-carboxamide, 2(R)-1-[4-(4-(Imidazol-4-yl)phenoxy)benzenesulfonyl]-N-hydroxy-hexahydro-1H-azepine-2-carboxamide, 2(R)-1-[4-(4-(Pyrazol-4-yl)phenoxy)benzenesulfonyl]-N-hydroxy-hexahydro-1H-azepine-2-carboxamide, 2(R)-1-[4-(4-(Pyrazol-3-yl)phenoxy)benzenesulfonyl]-N-hydroxy-hexahydro-1H-azepine-2-carboxamide, 2(R)-1-[4-(4-(2-(Dimethylamino)ethyl)phenoxy)benzenesulfonyl]-N-hydroxy-hexahydro-1H-azepine-2-carboxamide, 2(R)-1-[4-(Pyrid-4-yl)oxybenzenesulfonyl]-N-hydroxy-hexahydro-1H-azepine-2-carboxamide, 2(R), 3(S)-1-[4-(4-Chlorophenoxy)benzenesulfonyl]-N-hydroxy-3-methyl-hexahydro-1H-azepine-2-carboxamide, 2(R), 3(S)-1-[4-(4-Fluorophenoxy)benzenesulfonyl]-N-hydroxy-3-methyl-hexahydro-1H-azepine-2-carboxamide, 2(R), 3(S)-1-[4-(4-Methoxyphenoxy)benzenesulfonyl]-N-hydroxy-3-methyl-hexahydro-1H-azepine-2-carboxamide, 2(R), 3(S)-1-[4-(4-(Imidazol-1-yl)phenoxy)benzenesulfonyl]-N-hydroxy-3-methyl-hexahydro-1H-azepine-2-carboxamide, 2(R), 3(S)-1-[4-(4-(Imidazol-2-yl)phenoxy)benzenesulfonyl]-N-hydroxy-3-methyl-hexahydro-1H-azepine-2-carboxamide, 2(R), 3(S)-1-[4-(4-(Imidazol-4-yl)phenoxy)benzenesulfonyl]-N-hydroxy-3-methyl-hexahydro-1H-azepine-2-carboxamide, 2(R), 3(S)-1-[4-(4-(Pyrazol-4-yl)phenoxy)benzenesulfonyl]-N-hydroxy-3-methyl-hexahydro-1H-azepine-2-carboxamide, 2(R), 3(S)-1-[4-(4-(Pyrazol-3-yl)phenoxy)benzenesulfonyl]-N-hydroxy-3-methyl-hexahydro-1H-azepine-2-carboxamide, or 2(R), 3(S)-1-[4-(Pyrid-4-yl)oxybenzenesulfonyl]-N-hydroxy-3-methyl-hexahydro-1H-azepine-2-carboxamide;

or a pharmaceutically acceptable prodrug, salt, or solvate thereof.

13. A pharmaceutical composition comprising:

(a) a therapeutically effective amount of a compound as defined in claim 1 or a pharmaceutically acceptable prodrug, salt, or solvate thereof; and (b) a pharmaceutically acceptable carrier, diluent, vehicle, or excipient.

14. A method of treating a mammalian disease condition mediated by metalloproteinase activity which comprises administering to a mammal in need thereof a therapeutically effective amount of a compound as defined in claim 1 or a pharmaceutically acceptable prodrug, salt, or solvate thereof.

15. A method according to claim 14, wherein the mammalian disease condition is tumor growth, invasion, or metastasis.

16. A method according to claim 14, wherein the mammalian disease condition is osteoarthritis, rheumatoid arthritis, osteoporosis, periodontitis, or gingivitis.

17. A method according to claim 14, wherein the mammalian disease condition is chronic dermal wounds, corneal ulceration, or degenerative skin disorders.

18. A method according to claim 14, wherein the mammalian disease condition is multiple sclerosis or stroke.

19. A method according to claim 14, wherein the mammalian disease condition is atherosclerosis or glomerular disease.-

20. A method according to claim 14, wherein the mammalian disease condition is characterized by unwanted angiogenesis.

21. A method according to claim 14, wherein the mammalian disease condition is diabetic retinopathy, macular degeneration, angiofibromas, or hemangiomas.

22. A method according to claim 14, wherein the mammalian disease condition is mediated by matrix metalloproteinase activity.

23. A method according to claim 14, wherein the mammalian disease condition is mediated by TNF-α convertase activity.

24. A method of inhibiting the activity of at least one metalloproteinase which comprises contacting said at least one metalloproteinase with an effective amount of a compound as defined in claim 1 or a pharmaceutically acceptable prodrug, salt, or solvate thereof.

25. A method according to claim 24, wherein said at least one metalloproteinase is a matrix metalloproteinase.

26. A method according to claim 25, wherein said at least one metalloproteinase is a TNF-α convertase.

* * * * *